United States Patent [19]

Eisenschmid et al.

[11] Patent Number: 5,962,680
[45] Date of Patent: Oct. 5, 1999

[54] PROCESSES FOR PRODUCING EPSILON CAPROLACTAMS

[75] Inventors: Thomas Carl Eisenschmid, Cross Lanes; John Robert Briggs, Charleston; Diane Lee Packett, South Charleston; Kurt Damar Olson, Cross Lanes; John Michael Maher, Charleston, all of W. Va.

[73] Assignee: Union Carbide Chemicals & Plastics Technology Corporation, Danbury, Conn.

[21] Appl. No.: 08/839,576

[22] Filed: Apr. 15, 1997

[51] Int. Cl.[6] .................................................. C07D 201/08
[52] U.S. Cl. ............................................................ 540/538
[58] Field of Search ............................................... 540/538

[56] References Cited

U.S. PATENT DOCUMENTS

| | | | |
|---|---|---|---|
| 3,485,821 | 12/1969 | Sheehan | 260/239.3 |
| 3,652,549 | 3/1972 | Fujita et al. | 260/239.3 |
| 4,101,588 | 7/1978 | Nienburg et al. | 260/604 |
| 4,550,195 | 10/1985 | Platz et al. | 560/206 |
| 4,586,987 | 5/1986 | Schneider et al. | 560/206 |
| 4,622,423 | 11/1986 | Burke | 562/522 |
| 4,730,040 | 3/1988 | Vagt et al. | 540/538 |
| 4,730,041 | 3/1988 | Hutmacher et al. | 540/538 |
| 4,731,445 | 3/1988 | Hutmacher et al. | 540/538 |
| 4,801,738 | 1/1989 | Schneider et al. | 560/177 |
| 4,824,817 | 4/1989 | Drent | 502/154 |
| 4,879,405 | 11/1989 | Naeumann et al. | 560/211 |
| 4,894,474 | 1/1990 | Maerkl et al. | 560/206 |
| 4,910,328 | 3/1990 | Bertleff et al. | 560/177 |
| 4,925,972 | 5/1990 | Maerkl et al. | 560/206 |
| 4,933,487 | 6/1990 | Hoelderich et al. | 560/205 |
| 5,003,102 | 3/1991 | Bertleff et al. | 560/177 |
| 5,026,901 | 6/1991 | D'Amore | 560/207 |
| 5,028,734 | 7/1991 | Drent | 560/207 |
| 5,041,642 | 8/1991 | Jenck | 562/522 |
| 5,068,398 | 11/1991 | Merger et al. | 560/156 |
| 5,145,995 | 9/1992 | Burke | 562/522 |
| 5,159,107 | 10/1992 | Panitz et al. | 560/206 |
| 5,198,577 | 3/1993 | Denis et al. | 562/522 |
| 5,250,726 | 10/1993 | Burke | 562/522 |
| 5,264,616 | 11/1993 | Roeper et al. | 560/175 |
| 5,288,903 | 2/1994 | Bunel et al. | 562/598 |
| 5,292,944 | 3/1994 | Atadan et al. | 562/590 |
| 5,312,979 | 5/1994 | Denis et al. | 562/522 |
| 5,495,041 | 2/1996 | Sielcken et al. | 560/207 |

FOREIGN PATENT DOCUMENTS

| | | |
|---|---|---|
| 0556681 | 2/1903 | European Pat. Off. . |
| 0271145 | 11/1987 | European Pat. Off. . |
| 0273489 | 6/1988 | European Pat. Off. . |
| 0351616 | 1/1990 | European Pat. Off. . |
| 0405433 | 1/1991 | European Pat. Off. . |
| 0511126 | 4/1992 | European Pat. Off. . |
| 0562450 | 3/1993 | European Pat. Off. . |
| 0577205 | 6/1993 | European Pat. Off. . |
| 0643031 | 8/1994 | European Pat. Off. . |
| 0648731 | 4/1995 | European Pat. Off. . |
| 0662468 | 7/1995 | European Pat. Off. . |
| 0712828 | 11/1995 | European Pat. Off. . |
| 0738701 | 4/1996 | European Pat. Off. . |

(List continued on next page.)

OTHER PUBLICATIONS

Van Leeuwen, P.W.N.M. et al., "The Hydroformylation of Butadiene Catalysed by Rhodium–Diphosphine Complexes." Journal of Molecular Catalysis (31), 1985, pp. 345–353.

Botteghi, Carlo et al., "Optically Active Aldehydes via Hydroformylation of 1,3–Dienes with Chiral Diphosphinerhodium Complexes." Journal of Organometallic Chemistry (184), 1980, pp. C17–C19.

Bertozzi, Sergio et al., "Selective Hydroformylation of Open–chain Conjugated Dienes Promoted by Mesitylene–solvated Rhodium Atoms to give B,y Unsaturated Monoaldehydes." Journal of Organometallic Chemistry (487), 1995, pp. 41–45.

Fell, Bernhard et al., "The Hydroformylation of Conjugated Dienes, V* Aliphatic Tertiary Phosphines and P–Substituted Phospholanes as Cocatalysts of the Rhodium–Catalysed Hydroformylation of 1,3–Dienes." Journal of Molecular Catalysis (2), 1977, pp. 211–218.

Bahrmann, H. et al., "The Hydroformylation of Conjugated Dienes Vi* Tertiary Aryl–and Arylalkyl–Phosphines as Ligands in the Rhodium Catalyzed Hydroformylation Reaction of Conjugated Dienes to Dialdehydes." Journal of Molecular Catalysis (8), 1980, pp. 329–337.

Fell, Bernhard et al., "Reaction Products of a Hydroformylation of Conjugated Dienes with Rhodium Carbonyl/tert–Phosphine Catalyst Systems." Chemical–Zeitung (99), 1975, pp. 1–19.

Primary Examiner—Mukund J. Shah
Assistant Examiner—Bruck Kifle
Attorney, Agent, or Firm—Gerald L. Coon

[57] ABSTRACT

This invention relates in part to processes for producing one or more substituted or unsubstituted epsilon caprolactams, e.g., epsilon caprolactam, which comprises: (a) subjecting one or more substituted or unsubstituted alkadienes to hydroxycarbonylation in the presence of a hydroxycarbonylation catalyst, e.g., a metal-organophosphorus ligand complex catalyst, and neutralization with a base to produce one or more substituted or unsubstituted pentenoic acid salts; (b) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or said one or more substituted or unsubstituted epsilon caprolactam precursors to reductive amination in the presence of a reductive amination catalyst and cyclization optionally in the presence of a cyclization catalyst to produce said one or more substituted or unsubstituted epsilon caprolactams. This invention also relates in part to reaction mixtures containing one or more substituted or unsubstituted epsilon caprolactams as the principal product(s) of reaction.

22 Claims, No Drawings

FOREIGN PATENT DOCUMENTS

| | | |
|---|---|---|
| 0728732 | 8/1996 | European Pat. Off. . |
| 0729943 | 9/1996 | European Pat. Off. . |
| 0729944 | 9/1996 | European Pat. Off. . |
| 6306012 | 4/1993 | Japan . |
| 9426688 | 11/1994 | WIPO . |
| 9506025 | 3/1995 | WIPO . |
| 9506027 | 3/1995 | WIPO . |
| 9518089 | 7/1995 | WIPO . |
| 9518783 | 7/1995 | WIPO . |
| 9530680 | 11/1995 | WIPO . |
| 9616923 | 6/1996 | WIPO . |
| 9617817 | 6/1996 | WIPO . |
| 9702091 | 1/1997 | WIPO . |
| 9702228 | 1/1997 | WIPO . |
| 9703943 | 2/1997 | WIPO . |
| 9705949 | 2/1997 | WIPO . |
| 9708123 | 3/1997 | WIPO . |
| 9708127 | 3/1997 | WIPO . |

PROCESSES FOR PRODUCING EPSILON CAPROLACTAMS

BRIEF SUMMARY OF THE INVENTION

1. Technical Field

This invention relates in part to processes for producing one or more substituted or unsubstituted epsilon caprolactams. This invention also relates in part to reaction mixtures containing one or more substituted or unsubstituted epsilon caprolactams as the desired product(s) of reaction.

2. Background of the Invention

Epsilon caprolactam is a valuable intermediate which is useful, for example, in the production of nylon 6. The processes currently used to produce epsilon caprolactam have various disadvantages. For example, the prior art processes to epsilon caprolactam generate large amounts of byproducts, e.g., ammonium sulfate. Accordingly, it would be desirable to produce epsilon caprolactam from relatively inexpensive starting materials (e.g., butadiene) and by a process which does not have the disadvantages of prior art processes.

DISCLOSURE OF THE INVENTION

It has been discovered that alkadienes can be converted to epsilon caprolactams through a series of reactions involving certain salt intermediates. It has also been discovered that unsaturated acid salts, e.g., pentenoic acid salts, can be hydroformylated to aldehyde acid salts, e.g., 5-formylvaleric acid salts, in high selectivities, i.e., higher selectivities than obtained hydroformylating pentenoic acids to formylvaleric acids. In particular, it has been surprisingly discovered that such unsaturated acid salts possessing internal olefinic unsaturation can be hydroformylated to aldehyde acid salt products in high normal:branched isomer ratios, e.g., 3-pentenoic acid salts hydroformylated to 5-formylvaleric acid salts in high normal:branched isomer ratios. In addition, through the use of the salt intermediates in accordance with this invention, the acid catalyzed degradation of organophosphite ligands and/or deactivation of metal-organophosphite ligand complex catalysts can be prevented or minimized. In addition, the use of bases to prepare salts of unsaturated acids and/or aldehyde acids may facilitate recovery of products by, for example, phase separation or solvent extraction.

This invention relates to a process for producing one or more substituted or unsubstituted epsilon caprolactams, e.g., epsilon caprolactam, which comprises: (a) subjecting one or more substituted or unsubstituted alkadienes to hydroxycarbonylation in the presence of a hydroxycarbonylation catalyst, e.g., a metal-organophosphorus ligand complex catalyst, and neutralization with a base to produce one or more substituted or unsubstituted pentenoic acid salts; (b) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or said one or more substituted or unsubstituted epsilon caprolactam precursors to reductive amination in the presence of a reductive amination catalyst and cyclization optionally in the presence of a cyclization catalyst to produce said one or more substituted or unsubstituted epsilon caprolactams.

This invention also relates to a process for producing one or more substituted or unsubstituted epsilon caprolactams, e.g., epsilon caprolactam, which comprises: (a) subjecting one or more substituted or unsubstituted alkadienes to hydroxycarbonylation in the presence of a hydroxycarbonylation catalyst, e.g., a metal-organophosphorus ligand complex catalyst, to produce one or more substituted or unsubstituted pentenoic acids; (b) subjecting said one or more substituted or unsubstituted pentenoic acids to neutralization with a base to produce one or more substituted or unsubstituted pentenoic acid salts; (c) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said one or more substituted or unsubstituted epsilon caprolactams.

This invention further relates to a process for producing one or more substituted or unsubstituted epsilon caprolactams, e.g., epsilon caprolactam, which comprises: (a) subjecting one or more substituted or unsubstituted alkadienes to hydroxycarbonylation in the presence of a hydroxycarbonylation catalyst, e.g., a metal-organophosphorus ligand complex catalyst, and neutralization with ammonia to produce one or more substituted or unsubstituted pentenoic acid salts, e.g., ammonium 3-pentenoate; (b) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., ammonium 5-formylvalerate, and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive cyclization in the presence of a reductive cyclization catalyst to produce said one or more substituted or unsubstituted epsilon caprolactams.

This invention yet further relates to a process for producing one or more substituted or unsubstituted epsilon caprolactams, e.g., epsilon caprolactam, which comprises: (a) subjecting one or more substituted or unsubstituted alkadienes to hydroxycarbonylation in the presence of a hydroxycarbonylation catalyst, e.g., a metal-organophosphorus ligand complex catalyst, to produce one or more substituted or unsubstituted pentenoic acids; (b) subjecting said one or more substituted or unsubstituted pentenoic acids to neutralization with ammonia to produce one or more substituted or unsubstituted pentenoic acid salts, e.g., ammonium 3-pentenoate; (c) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., ammonium 5-formylvalerate, and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive cyclization in the presence of a reductive cyclization catalyst to produce said one or more substituted or unsubstituted epsilon caprolactams.

This invention also relates to a process for producing one or more substituted or unsubstituted aldehyde acid salts, e.g., formylvaleric acid salts such as triethylammonium 5-formylvalerate and ammonium 5-formylvalerate, and/or one or more substituted or unsubstituted epsilon caprolactam precursors which comprises subjecting one or more substituted or unsubstituted unsaturated acid salts, e.g., pentenoic acid salts such as triethylammonium 3-pentenoate and ammonium 3-pentenoate, to hydroformylation in the presence of a hydroformylation catalyst, e.g., a metal-organophosphorus ligand complex catalyst, to produce said one or more substituted or unsubstituted aldehyde acid salts andjor one or more substituted or unsubstituted epsilon caprolactam precursors.

This invention further relates in part to a process for producing a batchwise or continuously generated reaction mixture comprising:

(1) one or more substituted or unsubstituted epsilon caprolactams, e.g., epsilon caprolactam;

(2) optionally one or more substituted or unsubstituted formylvaleric acid salts, e.g., triethylammonium 5-formylvalerate and ammonium 5-formylvalerate, and/or one or more substituted or unsubstituted epsilon caprolactam precursors;

(3) optionally one or more substituted or unsubstituted pentenoic acid salts, e.g., triethylammonium 3-pentenoate and ammonium 3-pentenoate;

(4) optionally one or more substituted or unsubstituted pentenoic acids, e.g., cis-3-pentenoic acids, trans-3-pentenoic acids, 4-pentenoic acid, cis-2-pentenoic acids and/or trans-2-pentenoic acids; and (5) one or more substituted or unsubstituted butadienes, e.g., butadiene; wherein the weight ratio of component (1) to the sum of components (2), (3) and (4) is greater than about 0.1, preferably greater than about 0.25, more preferably greater than about 1.0; and the weight ratio of component (5) to the sum of components (1), (2), (3) and (4) is about 0 to about 100, preferably about 0.001 to about 50; which process comprises: (a) subjecting one or more substituted or unsubstituted butadienes to hydroxycarbonylation in the presence of a hydroxycarbonylation catalyst, e.g., a metal-organophosphorus ligand complex catalyst, and neutralization with a base to produce one or more substituted or unsubstituted pentenoic acid salts; (b) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said batchwise or continuously generated reaction mixture.

This invention yet further relates in part to a process for producing a batchwise or continuously generated reaction mixture comprising:

(1) one or more substituted or unsubstituted epsilon caprolactams, e.g., epsilon caprolactam;

(2) optionally one or more substituted or unsubstituted formylvaleric acid salts, e.g., triethylammonium 5-formylvalerate and ammonium 5-formylvalerate, and/or one or more substituted or unsubstituted epsilon caprolactam precursors;

(3) optionally one or more substituted or unsubstituted pentenoic acid salts, e.g., triethylammonium 3-pentenoate and ammonium 3-pentenoate;

(4) optionally one or more substituted or unsubstituted pentenoic acids, e.g., cis-3-pentenoic acids, trans-3-pentenoic acids, 4-pentenoic acid, cis-2-pentenoic acids and/or trans-2-pentenoic acids; and (5) one or more substituted or unsubstituted butadienes, e.g., butadiene; wherein the weight ratio of component (1) to the sum of components (2), (3) and (4) is greater than about 0.1, preferably greater than about 0.25, more preferably greater than about 1.0; and the weight ratio of component (5) to the sum of components (1), (2), (3) and (4) is about 0 to about 100, preferably about 0.001 to about 50;

which process comprises: (a) subjecting one or more substituted or unsubstituted butadienes to hydroxycarbonylation in the presence of a hydroxycarbonylation catalyst, e.g., a metal-organophosphorus ligand complex catalyst, to produce one or more substituted or unsubstituted pentenoic acids; (b) subjecting said one or more substituted or unsubstituted pentenoic acids to neutralization with a base to produce one or more substituted or unsubstituted pentenoic acid salts; (c) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said batchwise or continuously generated reaction mixture.

This invention also relates in part to a process for producing a batchwise or continuously generated reaction mixture comprising:

(1) one or more substituted or unsubstituted epsilon caprolactams, e.g., epsilon caprolactam;

(2) optionally one or more substituted or unsubstituted formylvaleric acid salts, e.g., ammonium 5-formylvalerate, and/or one or more substituted or unsubstituted epsilon caprolactam precursors;

(3) optionally one or more substituted or unsubstituted pentenoic acid salts, e.g., ammonium 3-pentenoate;

(4) optionally one or more substituted or unsubstituted pentenoic acids, e.g., cis-3-pentenoic acids, trans-3-pentenoic acids, 4-pentenoic acid, cis-2-pentenoic acids and/or trans-2-pentenoic acids; and (5) one or more substituted or unsubstituted butadienes, e.g., butadiene; wherein the weight ratio of component (1) to the sum of components (2), (3) and (4) is greater than about 0.1, preferably greater than about 0.25, more preferably greater than about 1.0; and the weight ratio of component (5) to the sum of components (1), (2), (3) and (4) is about 0 to about 100, preferably about 0.001 to about 50;

which process comprises: (a) subjecting one or more substituted or unsubstituted butadienes to hydroxycarbonylation in the presence of a hydroxycarbonylation catalyst, e.g., a metal-organophosphorus ligand complex catalyst, and neutralization with ammonia to produce one or more substituted or unsubstituted pentenoic acid salts, e.g., ammonium 3-pentenoate; (b) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., ammonium 5-formylvalerate, and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive cyclization in the presence of a reductive cyclization catalyst to produce said batchwise or continuously generated reaction mixture.

This invention further relates in part to a process for producing a batchwise or continuously generated reaction mixture comprising:

(1) one or more substituted or unsubstituted epsilon caprolactams, e.g., epsilon caprolactam;

(2) optionally one or more substituted or unsubstituted formylvaleric acid salts, e.g., ammonium 5-formylvalerate, and/or one or more substituted or unsubstituted epsilon caprolactam precursors;

(3) optionally one or more substituted or unsubstituted pentenoic acid salts, e.g., ammonium 3-pentenoate;

(4) optionally one or more substituted or unsubstituted pentenoic acids, e.g., cis-3-pentenoic acids, trans-3-pentenoic acids, 4-pentenoic acid, cis-2-pentenoic acids and/or trans-2-pentenoic acids; and (5) one or more substituted or unsubstituted butadienes, e.g., butadiene; wherein the weight ratio of component (1) to the sum of components (2), (3) and (4) is greater than about 0.1, preferably greater than about 0.25, more preferably greater than about 1.0; and the weight ratio of component (5) to the sum of components (1), (2), (3) and (4) is about 0 to about 100, preferably about 0.001 to about 50;

which process comprises: (a) subjecting one or more substituted or unsubstituted butadienes to hydroxycarbonylation in the presence of a hydroxycarbonylation catalyst, e.g., a metal-organophosphorus ligand complex catalyst, to produce one or more substituted or unsubstituted pentenoic acids; (b) subjecting said one or more substituted or unsubstituted pentenoic acids to neutralization with ammonia to produce one or more substituted or unsubstituted pentenoic acid salts, e.g., ammonium 3-pentenoate; (c) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., ammonium 5-formylvalerate, and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive cyclization in the presence of a reductive cyclization catalyst to produce said batchwise or continuously generated reaction mixture.

This invention yet further relates in part to a process for producing a batchwise or continuously generated reaction mixture comprising:

(1) one or more substituted or unsubstituted formylvaleric acid salts, e.g., triethylammonium 5-formylvalerate and ammonium 5-formylvalerate, and/or one or more substituted or unsubstituted epsilon caprolactam precursors;

(2) optionally one or more substituted or unsubstituted 4-formylvaleric acid salts and/or 3-formylvaleric acid salts;

(3) optionally one or more substituted or unsubstituted valeric acid salts; and (4) optionally one or more substituted or unsubstituted pentenoic acid salts, e.g., triethylammonium 3-pentenoate and ammonium 3-pentenoate; wherein the weight ratio of component (1) to the sum of components (2) and (3) is greater than about 0.1, preferably greater than about 0.25, more preferably greater than about 1.0; and the weight ratio of component (4) to the sum of components (1), (2) and (3) is about 0 to about 100, preferably about 0.001 to about 50;

which process comprises subjecting one or more substituted or unsubstituted pentenoic acid salts, e.g., triethylammonium 3-pentenoate and ammonium 3-pentenoate, to hydroformylation in the presence of a hydroformylation catalyst, e.g., a metal-organophosphorus ligand complex catalyst, to produce said batchwise or continuously generated reaction mixture.

This invention also relates to a process for producing a reaction mixture comprising one or more substituted or unsubstituted epsilon caprolactams, e.g., epsilon caprolactam, which process comprises: (a) subjecting one or more substituted or unsubstituted alkadienes to hydroxycarbonylation in the presence of a hydroxycarbonylation catalyst, e.g., a metal-organophosphorus ligand complex catalyst, and neutralization with a base to produce one or more substituted or unsubstituted pentenoic acid salts; (b) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said reaction mixture comprising one or more substituted or unsubstituted epsilon caprolactams.

This invention further relates to a process for producing a reaction mixture comprising one or more substituted or unsubstituted epsilon caprolactams, e.g., epsilon caprolactam, which process comprises: (a) subjecting one or more substituted or unsubstituted alkadienes to hydroxycarbonylation in the presence of a hydroxycarbonylation catalyst, e.g., a metal-organophosphorus ligand complex catalyst, to produce one or more substituted or unsubstituted pentenoic acids; (b) subjecting said one or more substituted or unsubstituted pentenoic acids to neutralization with a base to produce one or more substituted or unsubstituted pentenoic acid salts; (c) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said reaction mixture comprising one or more substituted or unsubstituted epsilon caprolactams.

This invention yet further relates to a process for producing a reaction mixture comprising one or more substituted or unsubstituted epsilon caprolactams, e.g., epsilon caprolactam, which process comprises: (a) subjecting one or more substituted or unsubstituted alkadienes to hydroxycarbonylation in the presence of a hydroxycarbonylation catalyst, e.g., a metal-organophosphorus ligand complex catalyst, and neutralization with ammonia to produce one or more substituted or unsubstituted pentenoic acid salts, e.g., ammonium 3-pentenoate; (b) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., ammonium 5-formylvalerate, and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive cyclization in the presence of a reductive cyclization catalyst to produce said reaction mixture comprising one or more substituted or unsubstituted epsilon caprolactams.

This invention also relates to a process for producing a reaction mixture comprising one or more substituted or unsubstituted epsilon caprolactams, e.g., epsilon caprolactam, which process comprises: (a) subjecting one or more substituted or unsubstituted alkadienes to hydroxycarbonylation in the presence of a hydroxycarbonylation catalyst, e.g., a metal-organophosphorus ligand complex catalyst, to produce one or more substituted or unsubstituted pentenoic acids; (b) subjecting said one or more substituted or unsubstituted pentenoic acids to neutralization with ammonia to produce one or more substituted or unsubstituted pentenoic acid salts, e.g., ammonium 3-pentenoate; (c) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., ammonium 5-formylvalerate, and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive cyclization in the presence of a reductive cyclization catalyst to produce said reaction mixture comprising one or more substituted or unsubstituted epsilon caprolactams.

This invention further relates to a process for producing a reaction mixture comprising one or more substituted or unsubstituted aldehyde acid salts, e.g., formylvaleric acid salts such as triethylammonium 5-formylvalerate and ammonium 5-formylvalerate, and/or one or more substituted or unsubstituted epsilon caprolactam precursors which process comprises subjecting one or more substituted or unsubstituted unsaturated acid salts, e.g., pentenoic acid salts such as triethylammonium 3-pentenoate and ammonium 3-pentenoate, to hydroformylation in the presence of a hydroformylation catalyst, e.g., a metal-organophosphorus ligand complex catalyst, to produce said reaction mixture comprising one or more substituted or unsubstituted aldehyde acid salts and/or one or more substituted or unsubstituted epsilon caprolactam precursors.

The processes of this invention can achieve high selectivities of butadiene to epsilon caprolactam. Selectivities of epsilon caprolactam of at least 10% by weight and up to 75% by weight or greater may be achieved by the processes of this invention.

This invention yet further relates in part to a batchwise or continuously generated reaction mixture comprising:

(1) one or more substituted or unsubstituted epsilon caprolactams, e.g., epsilon caprolactam;

(2) optionally one or more substituted or unsubstituted formylvaleric acid salts, e.g., triethylammonium 5-formylvalerate and ammonium 5-formylvalerate, and/or one or more substituted or unsubstituted epsilon caprolactam precursors;

(3) optionally one or more substituted or unsubstituted pentenoic acid salts, e.g., triethylammonium 3-pentenoate and ammonium 3-pentenoate;

(4) optionally one or more substituted or unsubstituted pentenoic acids, e.g., cis-3-pentenoic acids, trans-3-pentenoic acids, 4-pentenoic acid, cis-2-pentenoic acids and/or trans-2-pentenoic acids; and (5) one or more substituted or unsubstituted butadienes, e.g., butadiene; wherein the weight ratio of component (1) to the sum of components (2), (3) and (4) is greater than about 0.1, preferably greater than about 0.25, more preferably greater than about 1.0; and the weight ratio of component (5) to the sum of components (1), (2), (3) and (4) is about 0 to about 100, preferably about 0.001 to about 50.

This invention also relates in part to a batchwise or continuously generated reaction mixture comprising:

(1) one or more substituted or unsubstituted formylvaleric acid salts, e.g., triethylammonium 5-formylvalerate and ammonium 5-formylvalerate, and/or one or more substituted or unsubstituted epsilon caprolactam precursors;

(2) optionally one or more substituted or unsubstituted 4-formylvaleric acid salts and/or 3-formylvaleric acid salts;

(3) optionally one or more substituted or unsubstituted valeric acid salts; and (4) optionally one or more substituted or unsubstituted pentenoic acid salts, e.g., triethylammonium 3-pentenoate and ammonium 3-pentenoate;

wherein the weight ratio of component (1) to the sum of components (2) and (3) is greater than about 0.1, preferably greater than about 0.25, more preferably greater than about 1.0; and the weight ratio of component (4) to the sum of components (1), (2) and (3) is about 0 to about 100, preferably about 0.001 to about 50.

This invention further relates in part to a reaction mixture comprising one or more substituted or unsubstituted epsilon caprolactams, e.g., epsilon caprolactam, in which said reaction mixture is prepared by a process which comprises: (a) subjecting one or more substituted or unsubstituted alkadienes to hydroxycarbonylation in the presence of a hydroxycarbonylation catalyst, e.g., a metal-organophosphorus ligand complex catalyst, and neutralization with a base to produce one or more substituted or unsubstituted pentenoic acid salts; (b) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said reaction mixture comprising one or more substituted or unsubstituted epsilon caprolactams.

This invention yet further relates in part to a reaction mixture comprising one or more substituted or unsubstituted epsilon caprolactams, e.g., epsilon caprolactam, in which said reaction mixture is prepared by a process which comprises: (a) subjecting one or more substituted or unsubstituted alkadienes to hydroxycarbonylation in the presence of a hydroxycarbonylation catalyst, e.g., a metal-organophosphorus ligand complex catalyst, to produce one or more substituted or unsubstituted pentenoic acids; (b) subjecting said one or more substituted or unsubstituted pentenoic acids to neutralization with a base to produce one or more substituted or unsubstituted pentenoic acid salts; (c) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said reaction mixture comprising one or more substituted or unsubstituted epsilon caprolactams.

This invention also relates in part to a reaction mixture comprising one or more substituted or unsubstituted epsilon caprolactams, e.g., epsilon caprolactam, in which said reaction mixture is prepared by a process which comprises: (a) subjecting one or more substituted or unsubstituted alkadienes to hydroxycarbonylation in the presence of a hydroxycarbonylation catalyst, e.g., a metal-organophosphorus ligand complex catalyst, and neutralization with ammonia to produce one or more substituted or unsubstituted pentenoic acid salts, e.g., ammonium 3-pentenoate; (b) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., ammonium 5-formylvalerate, and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive cyclization in the presence of a reductive cyclization catalyst to produce said reaction mixture comprising one or more substituted or unsubstituted epsilon caprolactams.

This invention further relates in part to a reaction mixture comprising one or more substituted or unsubstituted epsilon caprolactams, e.g., epsilon caprolactam, in which said reaction mixture is prepared by a process which comprises: (a) subjecting one or more substituted or unsubstituted alkadienes to hydroxycarbonylation in the presence of a hydroxycarbonylation catalyst, e.g., a metal-organophosphorus ligand complex catalyst, to produce one or more substituted or unsubstituted pentenoic acids; (b) subjecting said one or more substituted or unsubstituted pentenoic acids to neutralization with ammonia to produce one or more substituted or unsubstituted pentenoic acid salts, e.g., ammonium 3-pentenoate; (c) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., ammonium 5-formylvalerate, and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive cyclization in the presence of a reductive cyclization catalyst to produce said reaction mixture comprising one or more substituted or unsubstituted epsilon caprolactams.

This invention yet further relates in part to a reaction mixture comprising one or more substituted or unsubstituted aldehyde acid salts, e.g., formylvaleric acid salts such as triethylammonium 5-formylvalerate and ammonium 5-formylvalerate, and/or one or more substituted or unsubstituted epsilon caprolactam precursors in which said reaction mixture is prepared by a process which comprises subjecting one or more substituted or unsubstituted unsaturated acid salts, e.g., pentenoic acid salts such as triethylammonium 3-pentenoate and ammonium 3-pentenoate, to hydroformylation in the presence of a hydroformylation catalyst, e.g., a metal-organophosphorus ligand complex catalyst, to produce said reaction mixture comprising one or more substituted or unsubstituted aldehyde acid salts and/or one or more substituted or unsubstituted epsilon caprolactam precursors.

The reaction mixtures of this invention are distinctive insofar as the processes for their preparation achieve the generation of high selectivities of epsilon caprolactams in a manner which can be suitably employed in a commercial process for the manufacture of epsilon caprolactam. In particular, the reaction mixtures of this invention are distinctive insofar as the processes for their preparation allow for the production of epsilon caprolactams in relatively high yields without generating large amounts of byproducts, e.g., ammonium sulfate.

DETAILED DESCRIPTION

Hydroxycarbonylation Stage or Step

The hydroxycarbonylation process of this invention involves converting one or more substituted or unsubstituted alkadienes, e.g., butadiene, to one or more substituted or unsubstituted unsaturated acids, e.g., cis-3-pentenoic acids, trans-3-pentenoic acids, 4-pentenoic acid, cis-2-pentenoic acids and/or trans-2-pentenoic acids, in one or more steps or stages. As used herein, the term "hydroxycarbonylation" is contemplated to include all permissible hydroxycarbonylation processes which involve converting one or more substituted or unsubstituted alkadienes to one or more substituted or unsubstituted unsaturated acids. A preferred hydroxycarbonylation process useful in this invention is disclosed in U.S. patent application Ser. No. ( ), filed on an even date herewith, the disclosure of which is incorporated herein by reference. In general, the hydroxycarbonylation step or stage comprises reacting one or more substituted or unsubstituted alkadienes with carbon monoxide and water in the presence of a catalyst and a promoter to produce one or more substituted or unsubstituted unsaturated acids.

The hydroxycarbonylation reaction mixtures employable herein typically includes any solution derived from any corresponding hydroxycarbonylation process that contains at least some amount of the following ingredients or components, i.e., the unsaturated acid product, a catalyst, unreacted alkadiene, carbon monoxide gas and water, said ingredients corresponding to those employed and/or produced by the hydroxycarbonylation process from whence the hydroxycarbonylation reaction mixture may be derived. It is to be understood that the hydroxycarbonylation reaction mixture compositions employable herein can and normally will contain minor amounts of additional ingredients such as those which have either been deliberately employed in the hydroxycarbonylation process or formed in situ during said process. Examples of such ingredients that can also be present include a promoter such as a carboxylic acid, and in situ formed type products, such as saturated or unsaturated hydrocarbons and/or unreacted isomerized olefins corresponding to the alkadiene starting materials, and byproducts, as well as other inert co-solvent type materials or hydrocarbon additives, if employed.

Alkadienes useful in the hydroxycarbonylation are known materials and can be prepared by conventional processes. Reaction mixtures comprising alkadienes may be useful herein. The amounts of alkadienes employed in the hydroxycarbonylation is not narrowly critical and can be any amounts sufficient to produce unsaturated acids, preferably in high selectivities and acceptable rates. Alkadienes may be fed either batchwise or continuously.

Illustrative substituted and unsubstituted alkadiene starting materials useful in the hydroxycarbonylation reaction include, but are not limited to, conjugated aliphatic diolefins represented by the formula:

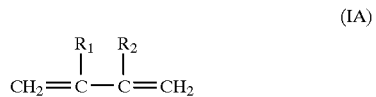

(IA)

wherein $R_1$ and $R_2$ are the same or different and are hydrogen, halogen or a substituted or unsubstituted hydrocarbon radical. The alkadienes can be linear or branched and can contain substituents (e.g., alkyl groups, halogen atoms, amino groups or silyl groups). Illustrative of suitable alkadiene starting materials are butadiene, isoprene, dimethyl butadiene and cyclopentadiene. Most preferably, the alkadiene starting material is butadiene itself ($CH_2$=CH—CH=$CH_2$). For purposes of this invention, the term "alkadiene" is contemplated to include all permissible substituted and unsubstituted conjugated diolefins, including all permissible mixtures comprising one or more substituted or unsubstituted conjugated diolefins. Illustrative of suitable substituted and unsubstituted alkadienes (including derivatives of alkadienes) include those permissible substituted and unsubstituted alkadienes described in Kirk-Othmer, Encyclopedia of Chemical Technology, Third Edition, 1984, the pertinent portions of which are incorporated herein by reference.

The catalysts useful in the hydroxycarbonylation process include, for example, Group 8, 9 and 10 metals or metal complexes (supported or unsupported), Group 8, 9 and 10 metal halides and esters (e.g., $PdCl_2$ and $PdI_2$), palladium bis(dibenzylidene acetone), Pd(OAc)$_2$, palladium on carbon, dicarbonylacetylacetonato rhodium (I), $RhCl_3$, $Co_2(CO)_8$, Group 8, 9 and 10 metal-ligand complex catalysts and the like. The hydroxycarbonylation catalysts may be in homogeneous or heterogeneous form. Such catalysts may be prepared by methods known in the art. Suitable metal-ligand complex catalysts useful in this invention are described more fully hereinbelow.

The permissible metals which make up the metal-ligand complex catalysts include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being palladium, rhodium, cobalt, iridium and ruthenium, more preferably palladium, rhodium, cobalt and ruthenium, especially palladium. The permissible ligands include, for example, organophosphorus, organoarsenic and organoantimony ligands, or mixtures thereof, preferably organophosphorus ligands. The permissible organophosphorus ligands which make up the metal-ligand complexes include organophosphines, e.g., mono-, di-, tri- and poly-(organophosphines), and organophosphites, e.g., mono-, di-, tri- and poly-(organophosphites). Other permissible organophosphorus ligands include, for example, organophosphonites, organophosphinites, amino phosphines and the like. Other permissible ligands include, for example, heteroatom-containing ligands such as 2,2'-bipyridyl and the like. Still other permissible ligands include, for example, heteroatom-containing ligands such as described in U.S. patent application Ser. No. 081,818,718, filed Mar. 10, 1997, the disclosure of which is incorporated herein by reference. Mixtures of such ligands may be employed if desired in the metal-ligand complex catalyst and/or free ligand and such mixtures may be the same or different. By "free ligand" is meant ligand that is not complexed with (tied to or bound to) the metal, e.g., palladium atom, of the complex catalyst. This invention is not intended to be limited in any manner by the permissible ligands or mixtures thereof. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

As noted the hydroxycarbonylation reactions involve the use of a metal-ligand complex catalyst as described herein. Of course mixtures of such catalysts can also be employed if desired. The amount of metal-ligand complex catalyst present in the reaction medium of a given hydroxycarbonylation reaction need only be that minimum amount necessary to provide the given metal concentration desired to be employed and which will furnish the basis for at least the catalytic amount of metal necessary to catalyze the particular hydroxycarbonylation reaction involved. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydroxycarbonylation reaction conditions and solvent employed.

In general, the organophosphorus ligand concentration in hydroxycarbonylation reaction mixtures may range from between about 0.005 and 25 weight percent based on the total weight of the reaction mixture. Preferably the ligand concentration is between 0.01 and 15 weight percent, and more preferably is between about 0.05 and 10 weight percent on that basis.

In general, the concentration of the metal in the hydroxycarbonylation reaction mixtures may be as high as about 2000 parts per million by weight or greater based on the weight of the reaction mixture. Preferably the metal concentration is between about 50 and 1500 parts per million by weight based on the weight of the reaction mixture, and more preferably is between about 70 and 1200 parts per million by weight based on the weight of the reaction mixture.

In addition to the metal-ligand complex catalyst, free ligand (i.e., ligand that is not complexed with the palladium metal) may also be present in the hydroxycarbonylation reaction medium. The free ligand may correspond to any of the above-defined ligands discussed above as employable herein. It is preferred that the free ligand be the same as the ligand of the metal-ligand complex catalyst employed. However, such ligands need not be the same in any given process. The hydroxycarbonylation reaction may involve up to 100 moles, or higher, of free ligand per mole of metal in the hydroxycarbonylation reaction medium. Preferably the hydroxycarbonylation reaction is carried out in the presence of from about 0.25 to about 50 moles of coordinatable phosphorus, and more preferably from about 0.5 to about 10 moles of coordinatable phosphorus per mole of metal present in the reaction medium; said amounts of coordinatable phosphorus being the sum of both the amount of coordinatable phosphorus that is bound (complexed) to the palladium metal present and the amount of free (non-complexed) coordinatable phosphorus present. Of course, if desired, make-up or additional coordinatable phosphorus can be supplied to the reaction medium of the hydroxycarbonylation reaction at any time and in any suitable manner, e.g. to maintain a predetermined level of free ligand in the reaction medium.

In an embodiment, the hydroxycarbonylation reaction involves converting butadiene in the liquid phase in the presence of carbon monoxide, water, palladium and an organic phosphorus, antimony or arsenic ligand to a reaction mixture comprising pentenoic acids, e.g., cis-3-pentenoic acids, trans-3-pentenoic acids, 4-pentenoic acid, cis-2-pentenoic acids and/or trans-2-pentenoic acids.

The palladium may be present in the reaction mixture as a heterogeneous palladium compound or as a homogeneous palladium compound. However, homogeneous systems are preferred. Since palladium in situ forms a complex with the ligand, the choice of the initial palladium compound is in general not critical. Examples of homogeneous palladium compounds are palladium salts of, for example, nitric acid, sulfonic acid, alkane carboxylic acids with not more than 12 carbon atoms or hydrogen halogenides (F, Cl, Br, I), but metallic palladium may also be used. Examples of such palladium compounds are $PdCl_2$, $PdBr_2$, $PdI_2$, $Na_2PdI_4$, $K_2PdI_4$, $PdCI_2$ (benzonitrile)$_2$ and bis(allylpalladium chloride). Another group of suitable halogen-free palladium compounds are palladium complexes such as palladium acetylacetonate ($Pd(acac)_2$), Pd(II) acetate, $Pd(NO_3)_2$, and palladium (benzylidene acetone)$_2$. An example of a suitable heterogeneous palladium compound is palladium on an ion exchange resin, such as for instance an ion exchange resin containing sulfonic acid groups.

The preferred ligand:palladium molar ratio is generally between about 1:1 and 10:1. When this ratio is lower, palladium can precipitate, whereas when this ratio is higher, the catalytic effect is weaker and byproducts such as vinyl cyclohexene and high molecular weight products can form. The optimum ratio will depend on the choice of the specific organic groups bounded to the phosphorus, arsenic or antimony atoms. The hydroxycarbonylation can optionally be carried out in the presence of one or more phosphine ligands. The phosphine:organophosphorus (e.g., organophosphite) ligand molar ratio may range between about 1:10 and 10:1.

When a complex of the ligand and palladium is separately prepared before being added to the hydroxycarbonylation reaction, an improved activity of the catalyst and an improved selectivity to the desired 3- and 4-pentenoic acids may occur compared to the situation in which this complex may be formed in situ. Such a complex of palladium and ligand, hereinafter called catalyst precursor, can be prepared by mixing a palladium compound as described above with the ligand. This mixing is preferably performed in a solvent. Temperature and pressure are not critical. The temperature can be, for example, between about 0° C. and 100° C. The pressure can be, for example, atmospheric pressure. The mixing is preferably performed in the absence of air. Examples of possible solvents include organic solvents, for example, benzene, toluene, xylene, or aliphatic solvents, for example, hexane, methyl pentenoate, methanol, acetone and ethanol, or the pentenoic acid products. Preferably the catalyst precursor is isolated from the mixture by crystallization of the catalyst precursor under, for example, atmospheric pressure. The solid catalyst precursor can be separated from the solvent by, for example, filtration or evaporation of the solvent. The solid catalyst precursor can be easily supplied to the hydroxycarbonylation reaction by, for example, dissolving the catalyst precursor in one of the reactants or solvents and supplying the resulting mixture to the reaction.

As indicated above, the hydroxycarbonylation is preferably carried out in the presence of a promoter. Suitable promoters include, for example, protonic organic acids, inorganic acids, Lewis acids, e.g., $BF_3$, and precursors capable of generating acids under hydroxycarbonylation conditions. The protonic organic acids are, for example, carboxylic acids and sulfonic acids with 1 to 30 carbon atoms. These carboxylic and sulfonic acids may be substituted with hydroxy, $C_1$–$C_4$ alkoxy, amine and halogenide groups, for example, chloride and bromide. Examples of preferred suitable carboxylic acids include benzoic acid or derived compounds, such as 2,4,6-trimethyl benzoic acid, meta- and parahydroxy benzoic acid, and product 3-and/or 4-pentenoic acids. Examples of preferred suitable sulfonic acids include methanesulfonic acid, trifluoromethane-sulfonic acid and para-toluenesulfonic acid. Example inorganic acids include HCl, HBr, $HBF_4$, $H_3PO_4$, $H_3PO_3$, $H_2SO_4$ and HI. Examples of materials capable of generating acidic promoters under hydroxycarbonylation conditions include ammonium and alkyl ammonium halides, alkali metal halides, organic acyl halides, and organosilylhalides. The amount of promoter is generally in the range of from about 1 to 10 mole equivalents per metal, e.g., palladium.

The particular hydroxycarbonylation reaction conditions are not narrowly critical and can be any effective hydroxycarbonylation conditions sufficient to produce the unsaturated acids. The reactors may be stirred tanks, tubular reactors and the like. The exact reaction conditions will be governed by the best compromise between achieving high catalyst selectivity, activity, lifetime and ease of operability, as well as the intrinsic reactivity of the alkadienes in question and the stability of the alkadienes and the desired reaction product to the reaction conditions. Products may be recovered after a particular reaction zone and purified if desired although preferably they are introduced to the next reaction zone without purification. Recovery and purification may be by any appropriate means, which will largely be determined by the particular alkadiene and catalyst employed, and may include distillation, phase separation, extraction, absorption, crystallization, derivative formation and the like. Of course, it is to be understood that the hydroxycarbonylation reaction conditions employed will be governed by the type of unsaturated acid product desired.

The hydroxycarbonylation process may be conducted at a total gas pressure of carbon monoxide and alkadiene starting compound of from about 1 to about 10,000 psia. In general, the hydroxycarbonylation process is operated at a total gas pressure of carbon monoxide and alkadiene starting compound of less than about 3000 psia and more preferably less than about 2000 psia, the minimum total pressure being limited predominately by the amount of reactants necessary to obtain a desired rate of reaction. The total pressure of the hydroxycarbonylation process will be dependent on the particular catalyst system employed. It is understood that carbon monoxide can be employed alone, in mixture with other gases, e.g., hydrogen, or may be produced in situ under reaction conditions.

Further, the hydroxycarbonylation process may be conducted at a reaction temperature from about 25° C. to about 300° C. In general, a hydroxycarbonylation reaction temperature of about 50° C. to about 200° C. is preferred for all types of alkadiene starting materials. The temperature must be sufficient for reaction to occur (which may vary with catalyst system employed), but not so high that ligand or catalyst decomposition occurs. At high temperatures (which may vary with catalyst system employed), the formation of undesired byproducts, e.g., vinylcyclohexene, may occur.

The quantity of water used is not narrowly critical. The water:butadiene molar equivalents ratio is generally between about 0.1:1 and 100:1, preferably between about 0.1:1 and 10:1, and more preferably between about 0.5:1 and 2:1. Preferably the molar ratio of water:butadiene is about 1:1. Water may be fed either batchwise or continuously.

The hydroxycarbonylation reactions may be conducted in the presence of water or an organic solvent. The solvent preferably does not react with the product unsaturated acids and will not itself be hydroxycarbonylated under the reaction conditions. Depending on the particular catalyst and reactants employed, suitable organic solvents include, for example, ethers, esters, ketones, aliphatic or aromatic hydrocarbons, fluorocarbons, silicones, polyethers, chlorinated hydrocarbons, carboxylic acids and the like. Any suitable solvent which does not unduly adversely interfere with the intended hydroxycarbonylation reaction can be employed and such solvents may include those disclosed heretofore commonly employed in known metal catalyzed hydroxycarbonylation reactions. Mixtures of one or more different solvents may be employed if desired. Illustrative preferred solvents employable in the production of unsaturated acids include ketones (e.g. acetone, methylethyl ketone and methylisobutyl ketone), esters (e.g. ethyl acetate, methyl acetate and butyrolactone), hydrocarbons (e.g. benzene, toluene and xylene), nitrohydrocarbons (e.g. nitrobenzene), ethers (e.g. diphenyl ether, dioxane, tetrahydrofuran (THF), glyme, anisole, trioxanone and diIsopropyl ether), sulfoxides and sulfones such as dimethyl sulfoxide and diisopropyl sulfone, and sulfolane. The amount of solvent employed is not critical to the subject invention and need only be that amount sufficient to facilitate the hydroxycarbonylation reaction and solubilize the catalyst and free ligand. In general, the amount of solvent may range from about 5 percent by weight up to about 99 percent by weight or more based on the total weight of the hydroxycarbonylation reaction mixture starting material.

In an embodiment of the invention, the hydroxycarbonylation reaction mixture may consist of one or more liquid phases, e.g. a polar and a nonpolar phase. Such processes are often advantageous in, for example, separating products from catalyst and/or reactants by partitioning into either phase. In addition, product selectivities dependent upon solvent properties may be increased by carrying out the reaction in that solvent. An illustrative application of this technology is the aqueous-phase hydroxycarbonylation of olefins employing sulfonated phosphine ligands for the palladium catalyst. A process carried out in aqueous solvent is particularly advantageous for the preparation of unsaturated acids because the products may be separated from the catalyst by extraction into an organic solvent.

As described herein, the phosphorus-containing ligand for the hydroxycarbonylation catalyst may contain any of a number of substituents, such as cationic or anionic substituents, which will render the catalyst soluble in a polar phase, e.g. water. Optionally, a phase-transfer catalyst may be added to the reaction mixture to facilitate transport of the catalyst, reactants, or products into the desired solvent phase. The structure of the ligand or the phase-transfer catalyst is not critical and will depend on the choice of conditions, reaction solvent, and desired products.

When the catalyst is present in a multiphasic system, the catalyst may be separated from the reactants and/or products by conventional methods such as extraction or decantation. The reaction mixture itself may consist of one or more phases; alternatively, the multiphasic system may be created at the end of the reaction by for example addition of a second solvent to separate the products from the catalyst. See, for example, U.S. Pat. No. 5,180,854, the disclosure of which is incorporated herein by reference.

The hydroxycarbonylation can be performed in the presence of organic nitrogen containing bases. The addition of these bases can be advantageous because they improve the catalyst stability. Examples of aromatic nitrogen containing bases include N-heterocyclic bases, for example, pyridine, alkylated pyridines, quinoline, lutidine, picoline, isoquinoline, alkylated quinolines and isoquinolines, acridine and N-methyl-2-pyrrolidinone or N,N-dimethylaniline, N,N-diethylaniline, N,N-diethyltoluidine, N,N-dibutyltoluidine, N,N-dimethylformamide, benzimidazole and benzotriazole. The amount of nitrogen containing base may range from about 0.1:1 or less to about 10:1 or greater based upon the unsaturated acid or salt.

In a preferred embodiment, the hydroxycarbonylation involves the preparation of pentenoic acids by hydroxycarbonylation of butadiene as described above wherein the following steps are performed:

(a) carbon monoxide, water, a source of palladium and an organophosphorus ligand and optionally a promoter and a solvent are continuously brought into a reactor in which the hydroxycarbonylation takes place;

(b) continuously separating part of the reaction mixture from the reactor;

(c) separating from the separated reaction mixture unreacted carbon monoxide, unreacted butadiene and unreacted water and returning these reactants to step (a), and isolating the pentenoic acids; and (d) returning the remaining mixture of step (c), containing palladium and the ligand and optionally the solvent and the promoter to step (a). Preferably a part of the remaining mixture of step (c) is separated from the mixture and led to a drain (purge) in order to prevent a build up of byproducts in the circulating reaction mixture.

Step (a) can be performed in several ways, for example, in a continuously stirred tank reactor or a bubble column in which the product is simultaneously stripped from the liquid phase.

Separating the carbon monoxide, butadiene, water and the pentenoic acids from the reaction mixture in step (c) can be performed in various ways. Generally the carbon monoxide is separated first from the reaction mixture in, for example, a simple gas-liquid separation unit. The butadiene, water and the pentenoic acids can be separated from the reaction mixture in one step followed by isolating the pentenoic acids from butadiene and water. Preferably the butadiene and water are separated from the reaction mixture in a separate step followed by the isolation of the pentenoic acids from the remaining reaction mixture. Separation of the various compounds can be performed in various ways, for example, by simple flash evaporation or by distillation. The choice as to which unit operation is the most suitable will depend on the physical properties of the compounds to be separated.

The ratio of the remaining mixture of step (c) which is returned to step (a) and the part which is processed to a drain will depend on the amount of contaminants (for example, byproducts) allowed in the recirculating reaction mixture. When a large part will be sent to the drain, a low degree of contamination in the recirculating reaction mixture will be the result and vice versa. The ratio of the remaining mixture of step (c) which is returned to step (a) and the part which is processed to a drain will depend on the amount of contamination formed in the hydroxycarbonylation and the acceptable level of contamination in the circulating process stream.

The part which is sent to the drain will contain apart from the above mentioned contaminants also the valuable palladium and ligand and optionally promoter and solvent (provided promoter and solvent are used in the hydroxycarbonylation). Preferably the palladium, ligand, acid product and solvent will be isolated from this mixture in order to advantageously reuse these compounds in the hydroxycarbonylation (step (a)). Examples of possible processes to separate these valuable compounds from some of the byproducts is by distillation, crystallization and extraction.

As indicated above, it may be desirable to carry out the hydroxycarbonylation process of this invention in a continuous manner. In general, continuous hydroxycarbonylation processes may involve: (a) hydroxycarbonylating the alkadiene starting material(s) with carbon monoxide and water in a liquid homogeneous reaction mixture comprising a solvent and the catalyst; (b) maintaining reaction temperature and pressure conditions favorable to the hydroxycarbonylation of the alkadiene starting material(s); (c) supplying make-up quantities of the alkadiene starting material(s), carbon monoxide and water to the reaction medium as those reactants are used up; and (d) recovering the desired unsaturated acid product(s) in any manner desired. The continuous process can be carried out in a single pass mode, i.e., wherein a vaporous mixture comprising unreacted alkadiene starting material(s) and vaporized unsaturated acid product is removed from the liquid reaction mixture from whence the unsaturated acid product is recovered and make-up alkadiene starting material(s), carbon monoxide and water are supplied to the liquid reaction medium for the next single pass through without recycling the unreacted alkadiene starting material(s). However, it may be desirable to employ a continuous process that involves either a liquid and/or gas recycle procedure. Such types of recycle procedure may involve the liquid recycling of the catalyst solution separated from the desired unsaturated acid reaction product or a gas cycle procedure, as well as a combination of both a liquid and gas recycle procedure if desired. Illustrative liquid and gas recycle procedures are disclosed in U.S. Pat. Nos.4,148,830 and 4,247,486, the disclosures of which are incorporated herein by reference.

In an embodiment of this invention, the unsaturated acid mixtures may be separated from the other components of the crude reaction mixtures in which the unsaturated acid mixtures are produced by any suitable method. Suitable separation methods include, for example, solvent extraction, crystallization, precipitation, distillation, vaporization, phase separation, wiped film evaporation, falling film evaporation and the like. A method for separating the unsaturated acid mixtures from the other components of the crude reaction mixtures is by membrane separation. Such membrane separation involving metal-ligand complex catalysts can be achieved as set out in U.S. Pat. No. 5,430,194 and copending U.S. patent application Ser. No. 08/430,790, filed May 5, 1995, both incorporated herein by reference. A crude reaction product can be subjected to a distillation-separation at atmospheric or reduced pressure through a packed distillation column. Reactive distillation may be useful in conducting the hydroxycarbonylation reaction.

The substituted and unsubstituted unsaturated acids that can be prepared by the hydroxycarbonylation process include, for example, alkenoic acids such as cis-3-pentenoic acids, trans-3-pentenoic acids, 4-pentenoic acid, cis-2-pentenoic acids and/or trans-2-pentenoic acids and the like. Illustrative of suitable substituted and unsubstituted unsaturated acid intermediates (including derivatives of substituted or unsubstituted unsaturated acid intermediates) include those permissible substituted and unsubstituted unsaturated acids which are described in Kirk-Othmer, Encyclopedia of Chemical Technology, Fourth Edition, 1996, the pertinent portions of which are incorporated herein by reference. The unsaturated acids described herein are useful in a variety of applications, such as chemical intermediates and the like.

The unsaturated acids produced by the hydroxycarbonylation step of this invention can be separated by conventional techniques such as distillation, extraction, precipitation, crystallization, membrane separation, phase separation or other suitable means. For example, a crude reaction product can be subjected to a distillation-separation at atmospheric or reduced pressure through a packed distillation column. Reactive distillation may be useful in conducting the hydroxycarbonylation reaction step. The subsequent neutralization of the unsaturated acid may be conducted without the need to separate the unsaturated acid from the other components of the crude reaction mixtures.

Neutralization Stage or Step

The neutralization process employed herein involves converting one or more substituted or unsubstituted unsaturated acids, e.g., pentenoic acids, to one or more substituted or unsubstituted unsaturated acid salts, e.g., pentenoic acid salts. As used herein, the term "neutralization" is contemplated to include, but is not limited to, all permissible neutralization processes which involve converting one or more substituted or unsubstituted unsaturated acids to one or more substituted or unsubstituted unsaturated acid salts. It is understood that neutralization may be conducted during the hydroxycarbonylation stage or step. In general, the neutralization step or stage comprises reacting one or more substituted or unsubstituted unsaturated acids with a base to produce one or more substituted or unsubstituted unsaturated acid salts.

In particular, one or more substituted or unsubstituted pentenoic acids can be reacted with a base to produce one or more substituted or unsubstituted pentenoic acid salts. For example, 3-pentenoic acid can be reacted with triethylamine to produce triethylammonium 3-pentenoate or with ammonia to produce ammonium 3-pentenoate. The neutralization of unsaturated acids to unsaturated acid salts may be carried out by conventional methods.

Unsaturated acids useful in the neutralization processes are known materials and can be prepared by the hydroxycarbonylation process described above or by conventional methods. Reaction mixtures comprising unsaturated acids may be useful herein. The amount of unsaturated acids employed in the neutralization step is not narrowly critical and can be any amount sufficient to produce pentenoic acid salts, preferably in high selectivities.

The base useful in the reaction of a pentenoic acid to a pentenoic acid salt is not narrowly critical. Illustrative bases include, for example, nitrogen containing bases (e.g., ammonia, trimethylamine, triethylamine, trioctylamine, ethyldioctylamine, tribenzylamine, diethylphenylamine, diphenylmethylamine, dimethylamine, diethanolamine, pyridine, bipyridine, benzimidazole, benzotriazole, ethylenediamine, and tetramethylethylenediamine), alkali metal hydroxides, alkoxides, carboxylates, carbonates and phosphates (e.g., sodium hydroxide, potassium hydroxide, lithium hydroxide, sodium methoxide, lithium butoxide, sodium carbonate, and potassium phosphate), ammonium or alkyl ammonium hydroxides and carboxylates (e.g. ammonium hydroxide, trimethylbutylammonium hydroxide, tetrabutylammonium hydroxide, trimethylbenzylammonium hydroxide, triethylphenylammonium acetate, and tetraethylammonium benzoate) alkyl phosphonium hydroxides and carboxylates, (e.g. octyltrimethylphosphonium hydroxide, tetrabutylphosponium hydroxide, ethyltriphenylphosphonium hydroxide, trimethylbenzylphosponium hydroxide), bis(hydrocarbyl-phosphine)iminium hydroxides, (e.g., bis(triphenylphosphine)iminium hydroxide, bis(tribenzylphosphine)iminium hydroxide). Alternatively, the base used for neutralization of the pentenoic acid may be incorporated into the ligand structure (e.g. tris(dimethylaminophenyl)-phosphine, bis(dimethylaminoethyl)phenylphosphine), either as the metal-ligand complex catalyst or as free ligand. The amount of base employed should be sufficient to neutralize, at least in part, the unsaturated acids.

The reactors and reaction conditions for the neutralization reaction steps are known in the art. The particular neutralization reaction conditions are not narrowly critical and can be any effective neutralization conditions sufficient to produce one or more unsaturated acid salts. The reactors may be stirred tanks, tubular reactors and the like. The exact reaction conditions will be governed by the best compromise between achieving high selectivity and ease of operability, as well as the intrinsic reactivity of the starting materials in question and the stability of the starting materials and the desired reaction product to the reaction conditions. Recovery and purification may be by any appropriate means, and may include distillation, phase separation, extraction, absorption, crystallization, derivative formation and the like.

The particular neutralization reaction conditions are not narrowly critical and can be any effective neutralization procedures sufficient to produce one or more unsaturated acid salts. For the reaction of unsaturated acids with a base, the temperature must be sufficient for reaction to occur but not so high that the unsaturated acids undergo undesirable side reactions, i.e., a temperature of from about 0° C. to about 200° C., preferably about 20° C. to about 100° C.

Illustrative substituted and unsubstituted unsaturated acid salts that can be prepared by the neutralization processes include one or more of the following: alkenoic acid salts such as triethylammonium 3-pentenoate, ammonium 3-pentenoate, octyltriethylammonium 3-pentenoate, including mixtures comprising one or more unsaturated acid salts. Illustrative of suitable substituted and unsubstituted unsaturated acid salts include those permissible substituted and unsubstituted unsaturated acid salts which are described in Kirk-Othmer, Encyclopedia of Chemical Technology, Fourth Edition, 1996, the pertinent portions of which are incorporated herein by reference.

The substituted and unsubstituted unsaturated acid salts produced by the neutralization steps of this invention can be separated by conventional techniques such as distillation, extraction, sublimation, precipitation, crystallization, membrane separation, phase separation or other suitable means. For example, a crude reaction product can be subjected to a distillation-separation at atmospheric or reduced pressure. Reactive distillation may be useful in conducting the neutralization reaction step. The subsequent hydroformylation of the unsaturated acid salt may be conducted without the need to separate the unsaturated acid salt from the other components of the crude reaction mixtures.

Hydroformylation Stage or Step

The hydroformylation processes involve the production of aldehyde acid salts, e.g., formylvaleric acid salts, and/or one or more substituted or unsubstituted epsilon caprolactam precursors by reacting an olefinic compound salt, e.g., pentenoic acid salt, with carbon monoxide and hydrogen in the presence of a solubilized metal-ligand complex catalyst and free ligand in a liquid medium that also contains a solvent for the catalyst and ligand. The processes may be carried out in a continuous single pass mode in a continuous gas recycle manner or more preferably in a continuous liquid catalyst recycle manner as described below. The hydroformylation processing techniques employable herein may correspond to any known processing techniques such as preferably employed in conventional liquid catalyst recycle hydroformylation reactions. As used herein, the term "hydroformylation" is contemplated to include, but is not limited to, all permissible hydroformylation processes which involve converting one or more substituted or unsubstituted olefinic compound salts to one or more substituted or unsubstituted aldehyde acid salts and/or one or more substituted or unsubstituted epsilon caprolactam precursors. In general, the hydroformylation step or stage comprises reacting one or more substituted or unsubstituted unsaturated acid salts with carbon monoxide and hydrogen in the presence of a catalyst to produce one or more substituted or unsubstituted aldehyde acid salts. As used herein, substituted or unsubstituted epsilon caprolactam precursors is contemplated to include, but are not limited to, one or more formylvaleric acid salts, iminocaproic acid and/or salts thereof, aminocaproic acid and/or salts thereof, caprolactam, caprolactone, imines, hemiaminals, imides, amides or amines derived from formylvaleric acid and its salts, and the corresponding dimers, trimers and oligomers.

The hydroformylation reaction mixtures employable herein includes any solution derived from any corresponding hydroformylation process that may contain at least some amount of four different main ingredients or components, i.e., the aldehyde acid salt product and/or epsilon caprolactam precursors, a metal-ligand complex catalyst, optionally free ligand and an organic solubilizing agent for said catalyst and said free ligand, said ingredients corresponding to those employed and/or produced by the hydroformylation process from whence the hydroformylation reaction mixture starting material may be derived. By "free ligand" is meant organophosphorus ligand that is not complexed with (tied to or bound to) the metal, e.g., rhodium atom, of the complex catalyst. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin salt starting material, carbon monoxide and hydrogen gases, and in situ formed type products, such as saturated hydrocarbons and/or unreacted isomerized olefins corresponding to the unsaturated acid salt starting materials, and high boiling liquid condensation byproducts, as well as other inert co-solvent type materials or hydrocarbon additives, if employed.

In an embodiment of this invention, certain additives can be employed in the hydroformylation reaction mixture to stabilize the organophosphorus ligands against degradation. For example, epoxides can be added to the hydroformylation reaction mixture to reduce degradation of the organophosphite ligand as described in U.S. Pat. No. 5,364,950, the disclosure of which is incorporated herein by reference.

The catalysts useful in the hydroformylation process include metal-ligand complex catalysts. The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. The permissible ligands include, for example, organophosphorus, organoarsenic and organoantimony ligands, or mixtures thereof, preferably organophosphorus ligands. The permissible organophosphorus ligands which make up the metal-ligand complexes include organophosphines, e.g., mono-, di-, tri- and poly-(organophosphines), and organophosphites, e.g., mono-, di-, tri- and poly-(organophosphites). Other permissible organophosphorus ligands include, for example, organophosphonites, organophosphinites, amino phosphines and the like. Still other permissible ligands include, for example, heteroatom-containing ligands such as described in U.S. patent application Ser. No. 081,898,918, filed Mar. 10, 1997, the disclosure of which is incorporated herein by reference. Mixtures of such ligands may be employed if desired in the metal-ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

The term "complex" as used herein and in the claims means a coordination compound formed by the union of one or more electronically rich molecules or atoms capable of independent existence with one or more electronically poor molecules or atoms, each of which is also capable of independent existence. For example, the ligands employable herein, i.e., organophosphorus ligands, may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, pentenoate, acetylacetonate, $SO_4$, $BF_4$, $PF_6$, $NO_2$, $NO_3$, $CH_3O$, $CH_2=CHCH_2$, $CH_2=CHCH_2CH_3$, $CH_3CH=CHCH_2$, $C_6H_5CN$, $CH_3CN$, NO, $NH_3$, pyridine, $(C_2H_5)_3N$, mono-olefins, diolefins and triolefins, tetrahydrofuran, and the like. It is of course to be understood that the complex species are preferably free of any additional organic ligand or anion that might poison the catalyst and have an undue adverse effect on catalyst performance. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one phosphorus-containing molecule complexed per metal, e.g., rhodium. As noted above, it is considered that the catalytic species of the preferred catalyst employed in the hydroformylation reaction may be complexed with carbon monoxide and hydrogen in addition to the organophosphorus ligands in view of the carbon monoxide and hydrogen gas employed by the hydroformylation reaction.

Among the organophosphines that may serve as the ligand of the metal-organophosphine complex catalyst and/or free organophosphine ligand of the hydroformylation reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl diphosphines and bisphosphine mono oxides, as well as ionic triorganophosphines containing at least one ionic moiety selected from the salts of sulfonic acid, of carboxylic acid, of phosphonic acid and of quaternary ammonium compounds, and the like. Of course any of the hydrocarbon radicals of such tertiary non-ionic and ionic organophosphines may be substituted if desired, with any suitable substituent that does not unduly adversely affect the desired result of the hydroformylation reaction. The organophosphine ligands employable in the hydroformylation reaction and/or methods for their preparation are known in the art.

Illustrative triorganophosphine ligands may be represented by the formula:

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, e.g., alkyl radicals, alkoxy radicals, silyl radicals such as —$Si(R^2)_3$; amino radicals such as —$N(R^2)_2$; acyl radicals such as —$C(O)R^2$; carboxy radicals such as —$C(O)OR^2$; acyloxy radicals such as —$OC(O)R^2$; amido radicals such as —$C(O)N(R^2)_2$ and —$N(R^2)C(O)R^2$; ionic radicals such as —$SO_3M$ wherein M represents inorganic or organic cationic atoms or radicals; sulfonyl radicals such as —SO₂R²; ether radicals such as —OR²; sulfinyl radicals such as —SOR²; sulfenyl radicals such as —SR² as well as halogen, nitro, cyano, trifluoromethyl and hydroxy radicals, and the like, wherein each R² individually represents the same or different substituted or unsubstituted monovalent hydrocarbon radical, with the proviso that in amino substituents such as —N(R²)₂, each R² taken together can also represent a divalent bridging group that forms a heterocyclic radical with the nitrogen atom and in amido substituents such as C(O)N(R²)₂ and —N(R²)C(O)R² each —R² bonded to N can also be hydrogen. Illustrative alkyl radicals include, e.g., methyl, ethyl, propyl, butyl and the like. Illustrative aryl radicals include, e.g., phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, e.g., triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, DIOP, i.e., (4R,5R)-(-)-O-isopropylidene-2,3-dihydroxy-1,4-bis(diphenylphosphino)butane and/or (4S,5S)-(+)-O-isopropylidene-2,3-dihydroxy-1,4-bis(diphenylphosphino)butane and/or (4S,5R)-(-)-O-isopropylidene-2,3-dihydroxy-1,4-bis(diphenylphosphino)butane, substituted or unsubstituted bicyclic bisphosphines such as 1,2-bis(1,4-cyclooctylenephosphino)ethane, 1,3-bis(1,4-cyclooctylenephosphino)propane, 1,3-bis(1,5-cyclooctylenephosphino)propane and 1,2-bis(2,6-dimethyl-1,4-cyclooctylenephosphino)ethane, substituted or unsubstituted bis(2,2'-diphenylphosphinomethyl)biphenyl such as bis(2,2'-diphenylphosphinomethyl)biphenyl and bis{2,2'-di(4-fluorophenyl)phosphinomethyl}biphenyl, xantphos, thixantphos, bis(diphenylphosphino)ferrocene, bis(diisopropylphosphino)ferrocene, bis(diphenylphosphino)ruthenocene, as well as the alkali and alkaline earth metal salts of sulfonated triphenylphosphines, e.g., of (tri-m-sulfophenyl)phosphine and of (m-sulfophenyl)diphenyl-phosphine and the like.

More particularly, illustrative metal-organophosphine complex catalysts and illustrative free organophosphine ligands include, e.g., those disclosed in U.S. Pat. Nos. 3,527,809; 4,148,830; 4,247,486; 4,283,562; 4,400,548; 4,482,749, 4,861,918; 4,694,109; 4,742,178; 4,851,581; 4,824,977; 5,332,846; 4,774,362; and WO Patent Application No. 95/30680, published Nov. 16, 1995; the disclosures of which are incorporated herein by reference.

The organophosphites that may serve as the ligand of the metal-organophosphite ligand complex catalyst and/or free ligand of the processes and reaction product mixtures of this invention may be of the achiral (optically inactive) or chiral (optically active) type and are well known in the art.

Among the organophosphites that may serve as the ligand of the metal-organophosphite complex catalyst and/or free organophosphite ligand of the hydroformylation reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

(II)

wherein R³ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, e.g., in U.S. Pat. No. 4,567,306, the disclosure of which is incorporated herein by reference.

Representative diorganophosphites may include those having the formula:

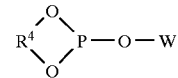

(III)

wherein R⁴ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by R⁴ include divalent acyclic radicals and divalent aromatic radicals. Illustrative divalent acyclic radicals include, e.g., alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, e.g., in U.S. Pat. Nos. 3,415,906 and 4,567,302 and the like, the disclosures of which are incorporated herein by reference. Illustrative divalent aromatic radicals include, e.g., arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably R⁴ is a divalent aromatic radical such as disclosed more fully, e.g., in U.S. Pat. Nos. 4,599,206 and 4,717,775, and the like, the disclosures of which are incorporated herein by reference.

Representative of a more preferred class of diorganophosphites are those of the formula:

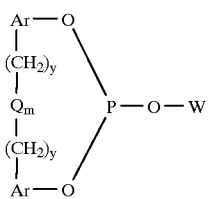
(IV)

wherein W is as defined above, each Ar is the same or different and represents a substituted or unsubstituted aryl radical, each y is the same or different and is a value of 0 or 1, Q represents a divalent bridging group selected from —C(R$^5$)$_2$—, —O—, —S—, —NR$^{6-}$, Si(R$^7$)$_2$— and —CO—, wherein each R$^5$ is the same or different and represents hydrogen, alkyl radicals having from 1 to 12 carbon atoms, phenyl, tolyl, and anisyl, R$^6$ represents hydrogen or a methyl radical, each R$^7$ is the same or different and represents hydrogen or a methyl radical, and mn is a value of 0 or 1. Such diorganophosphites are described in greater detail, e.g., in U.S. Pat. Nos. 4,599,206 and 4,717,775, the disclosures of which are incorporated herein by reference.

Representative triorganophosphites may include those having the formula:

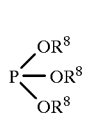
(V)

wherein each R$^8$ is the same or different and is a substituted or unsubstituted monovalent hydrocarbon radical, e.g., an alkyl or aryl radical. Suitable hydrocarbon radicals may contain from 1 to 24 carbon atoms or greater and may include those described above for R$^1$ in formula (I).

Representative organopolyphosphites contain two or more tertiary (trivalent) phosphorus atoms and may include those having the formula:

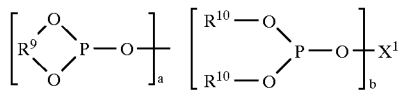
(VI)

wherein X$^1$ represents a substituted or unsubstituted n-valent hydrocarbon bridging radical containing from 2 to 40 carbon atoms, each R$^9$ is the same or different and is a divalent hydrocarbon radical containing from 4 to 40 carbon atoms, each R$^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each R$^9$ radical may be the same or different, and when b has a value of 1 or more, each R$^{10}$ radical may also be the same or different.

Representative n-valent (preferably divalent) hydrocarbon bridging radicals represented by X$^1$, as well as representative divalent hydrocarbon radicals represented by R$^9$ above, include both acyclic radicals and aromatic radicals, such as alkylene, alkylene-Q$_m$-alkylene, cycloalkylene, arylene, bisarylene, arylene-alkylene, and arylene-(CH$_2$)$_y$—Q$_m$—(CH$_2$)$_y$-arylene radicals, and the like, wherein Q, m and y are as defined above for formula (IV). The more preferred acyclic radicals represented by X$^1$ and R$^9$ above are divalent alkylene radicals, while the more preferred aromatic radicals represented by X$^1$ and R$^9$ above are divalent arylene and bisarylene radicals, such as disclosed more fully, e.g., in U.S. Pat. Nos. 3,415,906; 4,567,306; 4,599,206; 4,769,498; 4,717,775; 4,885,401; 5,202,297; 5,264,616 and 5,364,950, and the like, the disclosures of which are incorporated herein by reference. Representative monovalent hydrocarbon radicals represented by each R$^{10}$ radical above include alkyl and aromatic radicals.

Illustrative preferred organopolyphosphites may include bisphosphites such as those of formulas (VII) to (IX) below:

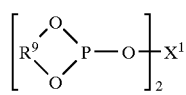
(VII)

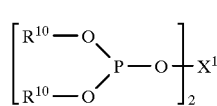
(VIII)

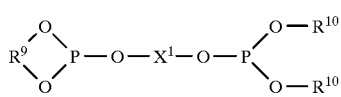
(IX)

wherein each R$^9$, R$^{10}$ and X$^1$ of formulas (VII) to (IX) are the same as defined above for formula (VI). Preferably, each R$^9$ and X$^1$ represents a divalent hydrocarbon radical selected from alkylene, arylene, arylene-alkylene-arylene, and bisarylene, while each R$^{10}$ represents a monovalent hydrocarbon radical selected from alkyl and aryl radicals. Phosphite ligands of such formulas (VI) to (IX) may be found disclosed, e.g., in said U.S. Pat. Nos. 4,668,651; 4,748,261; 4,769,498; 4,885,401; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

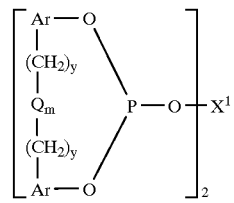
(X)

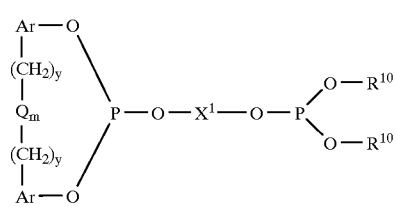
(XI)

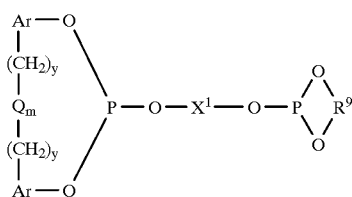

(XII)

wherein Ar, Q , $R^9$, $R^{10}$, $X^1$, m and y are as defined above. Most preferably $X^1$ represents a divalent aryl-$(CH_2)_y$—(Q)$_m$—$(CH_2)_y$-aryl radical wherein each y individually has a value of 0 or 1; m has a value of 0 or 1 and Q is —O—, —S— or —$C(R^5)_2$—wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulas. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organophosphite in the above formulas (VI) to (XII) may be an ionic phosphite, i.e., may contain one or more ionic moieties selected from the group consisting of:

$SO_3M$ wherein M represents an inorganic or organic cation, $PO_3M$ wherein M represents an inorganic or organic cation, $N(R^{11})_3X^2$ wherein each $R^{11}$ is the same or different and represents a hydrocarbon radical containing from 1 to 30 carbon atoms, e.g, alkyl, aryl, alkaryl, aralkyl, and cycloalkyl radicals, and $X^2$ represents an inorganic or organic anion, $CO_2M$ wherein M represents an inorganic or organic cation, as described, e.g., in U.S. Pat. Nos. 5,059,710; 5,113,022, 5,114,473 and 5,449,653, the disclosures of which are incorporated herein by reference. Thus, if desired, such phosphite ligands may contain from 1 to 3 such ionic moieties, while it is preferred that only one such ionic moiety be substituted on any given aryl moiety in the phosphite ligand when the ligand contains more than one such ionic moiety. As suitable counter-ions, M and $X^2$, for the anionic moieties of the ionic phosphites there can be mentioned hydrogen (i.e. a proton), the cations of the alkali and alkaline earth metals, e.g., lithium, sodium, potassium, cesium, rubidium, calcium, barium, magnesium and strontium, the ammonium cation, quaternary ammonium cations, phosphonium cations, arsonium cations and iminium cations. Suitable anionic atoms or radicals include, for example, sulfate, carbonate, phosphate, chloride, acetate, oxalate and the like.

Of course any of the $R^9$, $R^{10}$, $X^2$ and Ar radicals of such non-ionic and ionic organophosphites of formulas (VI) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —$Si(R^{12})_3$; amino radicals such as —$N(R^{12})_2$; phosphine radicals such as —aryl—$P(R^{12})_2$; acyl radicals such as —$C(O)R^{12}$; acyloxy radicals such as —$OC(O)R^{12}$; amido radicals such as —$CON(R^{12})_2$ and —$N(R^{12})COR^{12}$; sulfonyl radicals such as —$SO_2R^{12}$; alkoxy radicals such as —$OR^{12}$; sulfinyl radicals such as —$SOR^{12}$; sulfenyl radicals such as —$SR^{12}$; phosphonyl radicals such as —$P(O)(R^{12})_2$; as well as, halogen, nitro, cyano, trifluoromethyl, hydroxy radicals, and the like, wherein each $R^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —$N(R^{12})_2$ each $R^{12}$ taken together can also represent a divalent bridging group that forms a heterocyclic radical with the nitrogen atom, and in amido substituents such as —$C(O)N(R^{12})_2$ and —$N(R^{12})COR^{12}$ each $R^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —$OCH_2CH_2OCH_3$, —$(OCH_2CH_2)_2OCH_3$, —$(OCH_2CH_2)_3OCH_3$, and the like; aryloxy radicals such as phenoxy and the like; as well as silyl radicals such as —

$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; arylphosphine radicals such as —$P(C_6H_5)_2$, and the like; acyl radicals such as —$C(O)CH_3$, —$C(O)C_2H_5$, —$C(O)C_6H_5$, and the like; carbonyloxy radicals such as —$C(O)OCH_3$ and the like; oxycarbonyl radicals such as —$O(CO)C_6H_5$, and the like; amido radicals such as —$CONH_2$, —$CON(CH_3)_2$, —$NHC(O)CH_3$, and the like; sulfonyl radicals such as —$S(O)_2C_2H_5$ and the like; sulfinyl radicals such as —$S(O)CH_3$ and the like; sulfenyl radicals such as —$SCH_3$, —$SC_2H_5$, —$SC_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H_5)$, and the like.

Specific illustrative examples of such organophosphite ligands include the following: 2-t-butyl-4-methoxyphenyl(3,3'-di-t-butyl-5,5'-dimethoxy-1,1'-biphenyl-2,2'-diyl)phosphite having the formula:

Ligand A

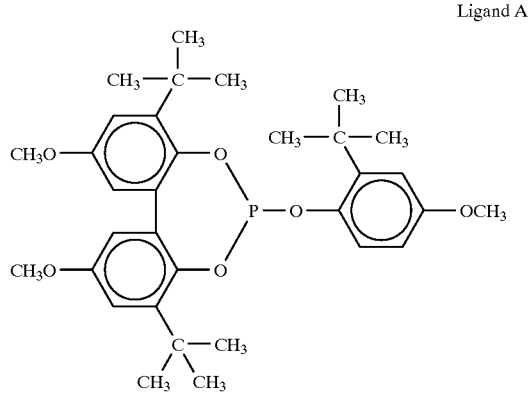

methyl(3,3'-di-t-butyl-5,5'-dimethoxy-1,1'-biphenyl-2,2'-diyl)phosphite having the formula:

Ligand B

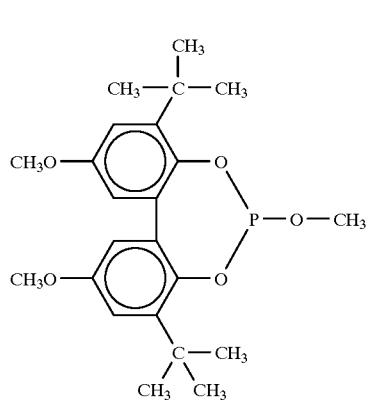

6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

Ligand C

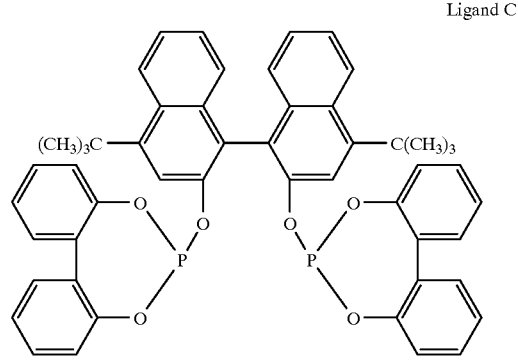

6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin having the formula:

Ligand D

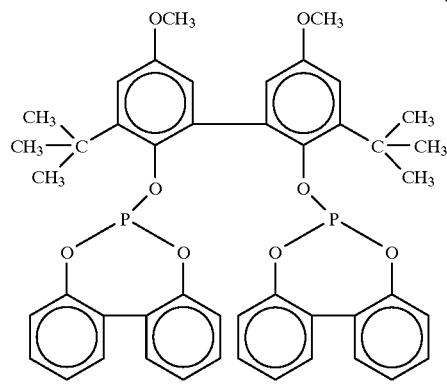

6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

Ligand E

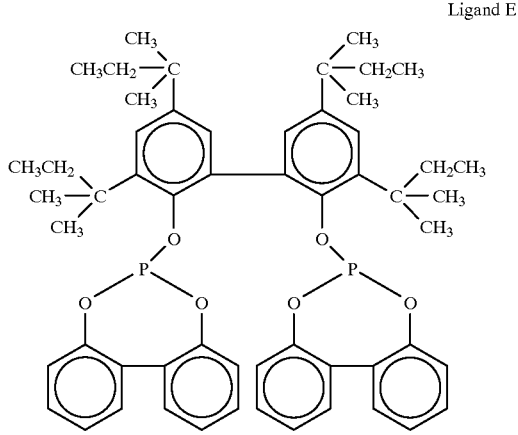

6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin having the formula:

Ligand F

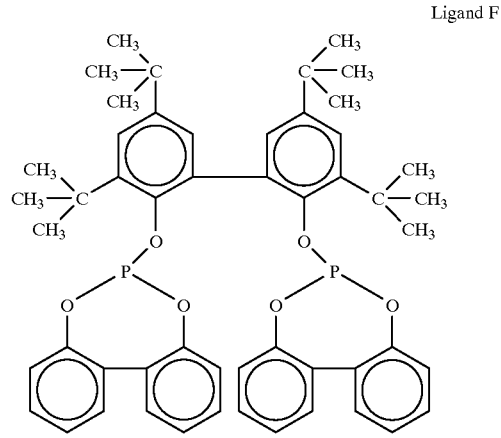

(2R,4R)-di[2,2'-(3,3',5,5'-tetrakis-tert-amyl-1,1'-biphenyl)]-2,4-pentyldiphosphite having the formula:
Ligand G
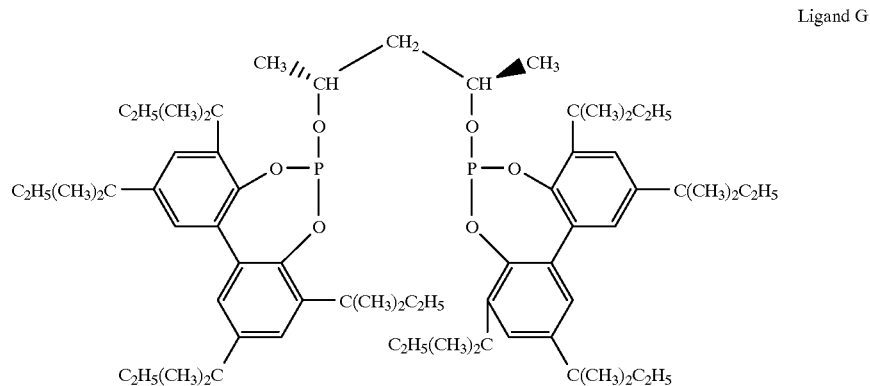
(2R,4R)-di[2,2'-(3,3',5,5'-tetrakis-tert-butyl-1,1'-biphenyl)]-2,4-pentyldiphosphite having the formula:
Ligand H
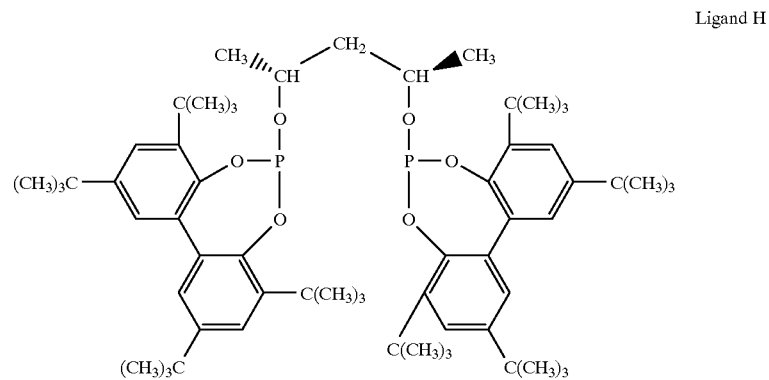
(2R,4R)-di[2,2'-(3,3'-di-amyl-5,5'-dimethoxy-1,1'-biphenyl)]-2,4-pentyldiphosphite having the formula:
Ligand I
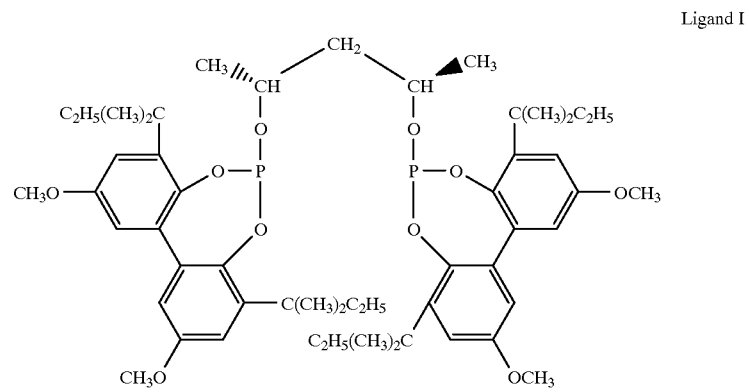

(2R,4R)-di[2,2'-(3,3'-di-tert-butyl-5,5'-dimethyl-1,1'-biphenyl)]-2,4-pentyldiphosphite having the formula:
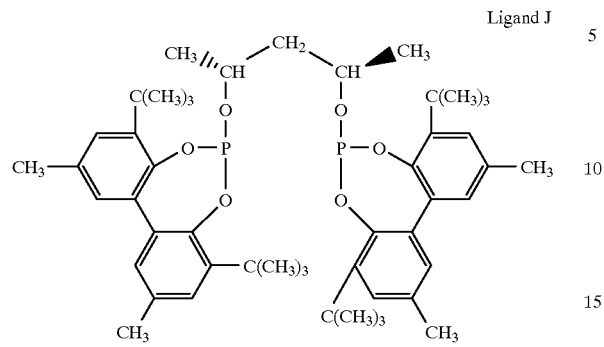
Ligand J
(2R,4R)-di[2,2'-(3,3'-di-tert-butyl-5,5'-diethoxy-1,1'-biphenyl)]-2,4-pentyldiphosphite having the formula:
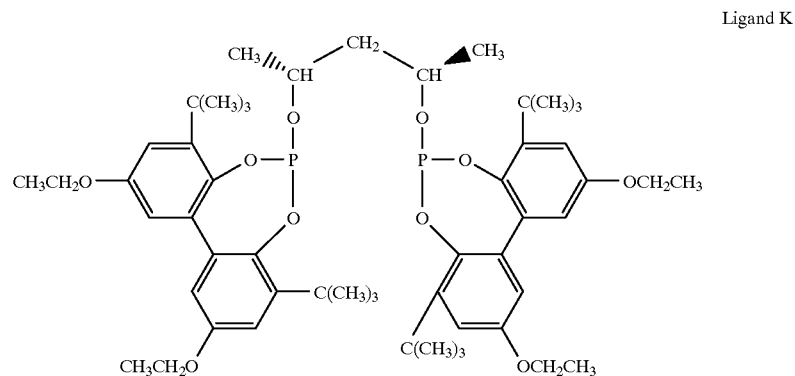
Ligand K
(2R,4R)-di[2,2'-(3,3'-di-tert-butyl-5,5'-diethyl-1,1'-biphenyl)]-2,4-pentyldiphosphite having the formula:
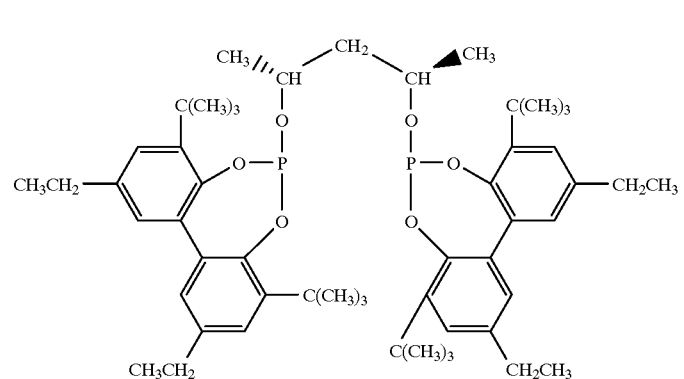
Ligand L (2R,4R)-di[2,2'-(3,3'-di-tert-butyl-5,5'-dimethoxy-1,1'-biphenyl)]-2,4-pentyldiphosphite having the formula:
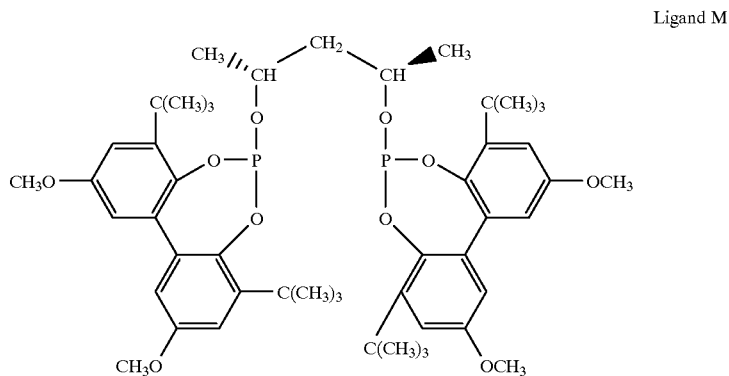
Ligand M
6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:
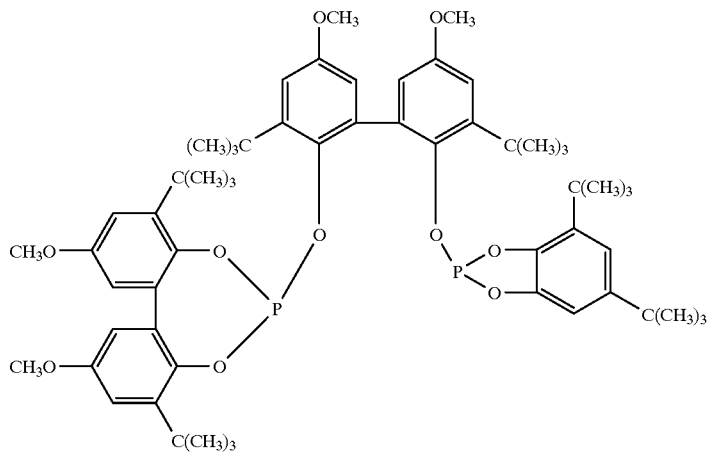
Ligand N 6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:
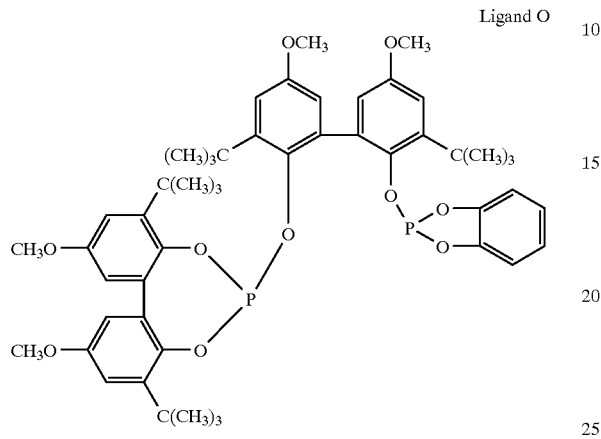
Ligand O
6-[[2'-[(5,5-dimethyl-1,3,2-dioxaphosphorinan-2-yl)oxy]-3,3'-bis(1,1-dimethylethyl)-5,5'-dimethoxy[1, 1'-biphenyl]-2-yl]oxy]-4,8-bis(1,1-dimethylethyl)-2,10-dimethoxydibenzo[d,f][1,3,2]dioxaphosphepin having the formula:
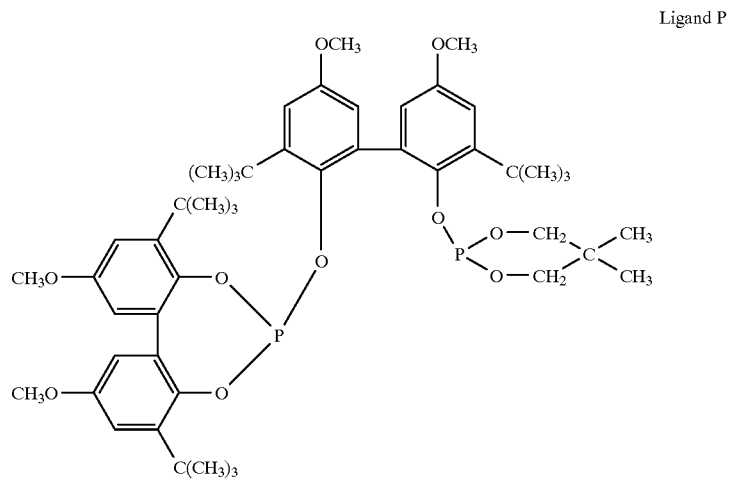
Ligand P 2'-[[4,8-bis(1,1-dimethylethyl)-2,10-dimethoxydibenzo[d,f]
[1,3,2]-dioxaphosphepin-6-yl]oxy]-3,3'-bis(1,1-
dimethylethyl)-5,5'-dimethoxy[1,1'-biphenyl]-2-yl bis(4-
hexylphenyl)ester of phosphorous acid having the formula:

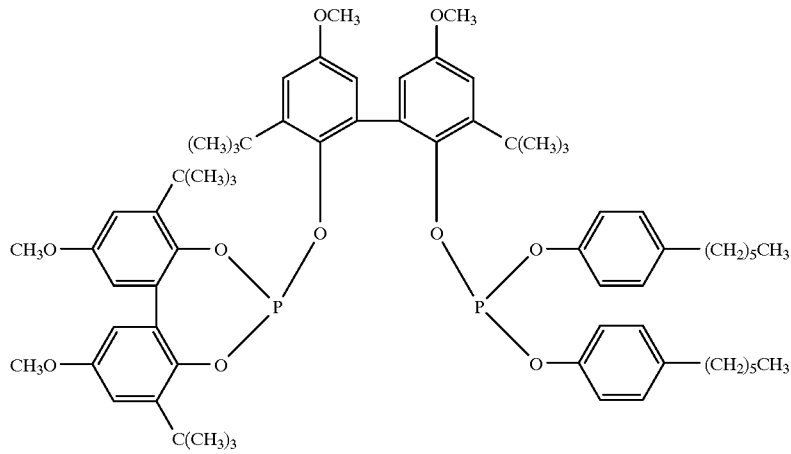

Ligand Q

2-[[2-[[4,8-bis(1,1-dimethylethyl), 2,10-dimethoxydibenzo-
[d,f][1,3,2]dioxophosphepin-6-yl]oxy]-3-(1,1-
dimethylethyl)-5-methoxyphenyl]methyl]-4-methoxy, 6-(1,
1-dimethylethyl)phenyl diphenyl ester of phosphorous acid
having the formula:

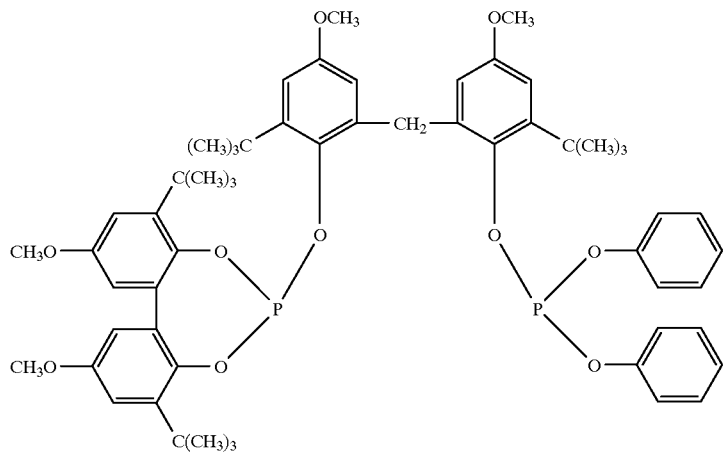

Ligand R 3-methoxy-1,3-cyclohexamethylene tetrakis[3,6-bis(1,1-dimethylethyl)-2-naphthalenyl]ester of phosphorous acid having the formula:

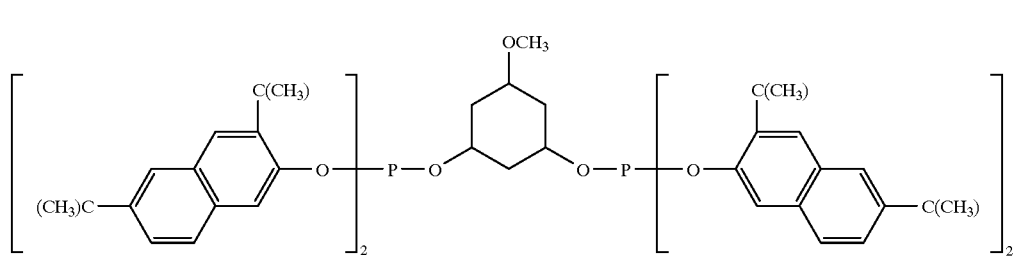

Ligand S 2,5-bis(1,1-dimethylethyl)-1,4-phenylene tetrakis[2,4-bis(1,1-dimethylethyl)phenyl]ester of phosphorous acid having the formula:

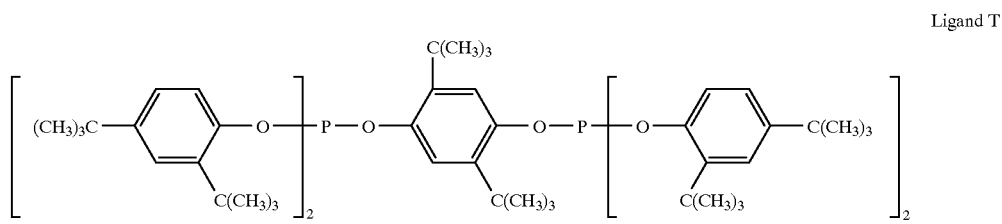

Ligand T methylenedi-2,1-phenylene tetrakis[2,4-bis(1,1-dimethylethyl)phenyl]ester of phosphorous acid having the formula:

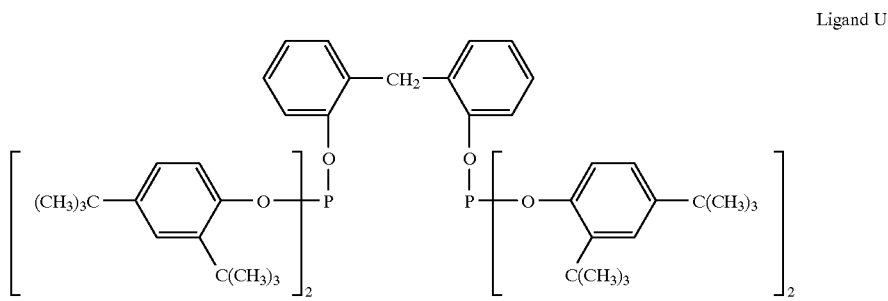

Ligand U

[1,1'-biphenyl]-2,2'-diyl tetrakis[2-(1,1-dimethylethyl)-4-methoxyphenyl]ester of phosphorous acid having the formula:

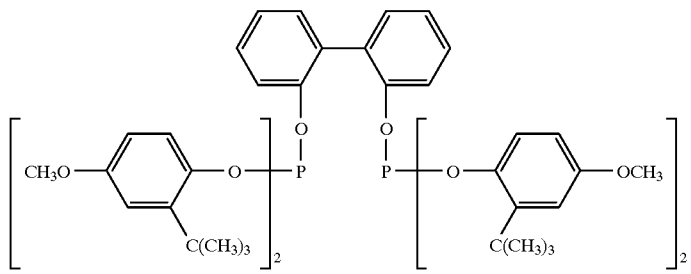

Ligand V

Still other illustrative organophosphorus ligands useful in this invention include those disclosed in U.S. patent application Ser. No. (D-17459-1), filed on an even date herewith, the disclosure of which is incorporated herein by reference.

The metal-ligand complex catalysts employable in this invention may be formed by methods known in the art. The metal-ligand complex catalysts may be in homogeneous or heterogeneous form. For instance, preformed metal hydrido-carbonyl-organophosphorus ligand catalysts may be prepared and introduced into the reaction mixture of a hydroformylation process. More preferably, the metal-ligand complex catalysts can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a solvent with the organophosphorus ligand to form a catalytic rhodium-organophosphorus ligand complex precursor which is introduced into the reactor along with excess free organophosphorus ligand for the in situ formation of the active catalyst. In any event, it is sufficient for the purpose of this invention that carbon monoxide, hydrogen and organophosphorus compound are all ligands that are capable of being complexed with the metal and that an active metal-organophosphorus ligand catalyst is present in the reaction mixture under the conditions used in the hydroformylation reaction.

More particularly, a catalyst precursor composition can be formed consisting essentially of a solubilized metal-organophosphorus ligand complex precursor catalyst, an organic solvent and free organophosphorus ligand. Such precursor compositions may be prepared by forming a solution of a metal starting material, such as a metal oxide, hydride, carbonyl or salt, e.g. a nitrate, which may or may not be in complex combination with a ligand as defined herein. Any suitable metal starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial metal, may be complexed to the metal either prior to or in situ during the hydroformylation process.

By way of illustration, the preferred catalyst precursor composition of this invention consists essentially of a solubilized rhodium carbonyl organophosphorus ligand complex precursor catalyst, a solvent and free organophosphorus ligand prepared by forming a solution of rhodium dicarbonyl acetylacetonate, an organic solvent and a ligand as defined herein. The organophosphorus ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorus ligand complex precursor are soluble can be employed. The amounts of rhodium complex catalyst precursor, organic solvent and organophosphorus ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphorus ligand, to form the active complex catalyst as explained above. In a continuous process, the acetylacetone which is freed from the precursor catalyst under hydroformylation conditions is removed from the reaction medium with the product aldehyde salt and thus is in no way detrimental to the hydroformylation process. The use of such preferred rhodium complex catalytic precursor compositions provides a simple economical and efficient method for handling the rhodium precursor metal and hydroformylation start-up.

Accordingly, the metal-ligand complex catalysts used in the process of this invention consists essentially of the metal complexed with carbon monoxide and a ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organophosphorus ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants. The hydrogen and/or carbonyl ligands of an active metal-ligand complex catalyst may be present as a result of being ligands bound to a precursor catalyst and/or as a result of in situ formation, e.g., due to the hydrogen and carbon monoxide gases employed in hydroformylation process of this invention.

As noted the hydroformylation reactions involve the use of a metal-ligand complex catalyst as described herein. Of course mixtures of such catalysts can also be employed if desired. The amount of metal-ligand complex catalyst present in the reaction medium of a given hydroformylation reaction need only be that minimum amount necessary to provide the given metal concentration desired to be employed and which will furnish the basis for at least the catalytic amount of metal necessary to catalyze the particular hydroformylation reaction involved such as disclosed e.g. in the above-mentioned patents. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydroformylation reaction conditions and solvent employed.

In general, the organophosphorus ligand concentration in hydroformylation reaction mixtures may range from between about 0.005 and 25 weight percent based on the total weight of the reaction mixture. Preferably the ligand concentration is between 0.01 and 15 weight percent, and more preferably is between about 0.05 and 10 weight percent on that basis.

In general, the concentration of the metal in the hydroformylation reaction mixtures may be as high as about 2000 parts per million by weight or greater based on the weight of the reaction mixture. Preferably the metal concentration is between about 50 and 1000 parts per million by weight based on the weight of the reaction mixture, and more preferably is between about 70 and 800 parts per million by weight based on the weight of the reaction mixture.

In addition to the metal-ligand complex catalyst, free ligand (i.e., ligand that is not complexed with the metal) may also be present in the hydroformylation reaction medium. The free ligand may correspond to any of the above-defined ligands discussed above as employable herein. It is preferred that the free ligand be the same as the ligand of the metal-ligand complex catalyst employed. However, such ligands need not be the same in any given process. The hydroformylation reaction may involve up to 100 moles, or higher, of free ligand per mole of metal in the hydroformylation reaction medium. Preferably the hydroformylation reaction is carried out in the presence of from about 0.25 to about 50 moles of coordinatable phosphorus, and more preferably from about 0.5 to about 30 moles of coordinatable phosphorus per mole of metal present in the reaction medium; said amounts of coordinatable phosphorus being the sum of both the amount of coordinatable phosphorus that is bound (complexed) to the metal present and the amount of free (non-complexed) coordinatable phosphorus present. Of course, if desired, make-up or additional coordinatable phosphorus can be supplied to the reaction medium of the hydroformylation reaction at any time and in any suitable manner, e.g. to maintain a predetermined level of free ligand in the reaction medium.

As indicated above, the hydroformylation catalyst may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

As an illustration, the rhodium catalyst may be impregnated onto any solid support, such as inorganic oxides, (e.g., alumina, silica, titania, or zirconia) carbon, or ion exchange resins. The catalyst may be supported on, or intercalated inside the pores of, a zeolite or glass; the catalyst may also be dissolved in a liquid film coating the pores of said zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: J. Mol. Cat. 1991, 70, 363–368; Catal. Lett. 1991, 8, 209–214; J. Organomet. Chem, 1991, 403, 221–227; Nature, 1989, 339, 454–455; J. Catal. 1985, 96, 563–573; J. Mol. Cat. 1987, 39, 243–259.

The rhodium catalyst may be attached to a thin film or membrane support, such as cellulose acetate or polyphenylenesulfone, as described in for example J. Mol. Cat. 1990, 63, 213–221.

The rhodium catalyst may be attached to an insoluble polymeric support through an organophosphorus-containing ligand, such as a phosphine or phosphite, incorporated into the polymer. Such polymer-supported ligands are well known, and include such commercially available species as the divinylbenzene/polystyrene-supported triphenylphosphine. The supported ligand is not limited by the choice of polymer or phosphorus-containing species incorporated into it. Descriptions of polymer-supported catalysts may be found in for example: J. Mol. Cat. 1993, 83, 17–35; Chemtech 1983, 46; J. Am. Chem. Soc. 1987, 109, 7122–7127.

In the heterogeneous catalysts described above, the catalyst may remain in its heterogeneous form during the entire hydroformylation and catalyst separation process. In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730.

When the rhodium catalyst is in a heterogeneous or supported form, the reaction is carried out in the slurry phase due to the high boiling points of the products, and to avoid decomposition of the product aldehyde salts. The catalyst may then be separated from the product mixture by filtration or decantation.

Pentenoic acid salts useful in the hydroformylation processes are known materials and can be prepared by the hydroxycarbonylation and neutralization steps described above or by conventional methods. Reaction mixtures comprising pentenoic acid salts may be useful herein. The amount of pentenoic acid salts employed in the hydroformylation step is not narrowly critical and can be any amount sufficient to produce formylvaleric acid salts, preferably in high selectivities.

The hydroformylation reaction conditions may include any suitable type hydroformylation conditions heretofore employed for producing aldehydes. For instance, the total gas pressure of hydrogen, carbon monoxide and other components of the hydroformylation process may range from about 1 to about 10,000 psia. In general, the hydroformylation process is operated at a total gas pressure of hydrogen, carbon monoxide and all other components of less than about 1500 psia and more preferably less than about 1000 psia, the minimum total pressure being limited predominately by the amount of reactants necessary to obtain a desired rate of reaction. The total pressure employed in the hydroformylation reaction may range in general from about 20 to about 3000 psia, preferably from about 50 to 2000 psia and more preferably from about 75 to about 1000 psia. The total pressure of the hydroformylation process will be dependent on the particular catalyst system employed.

More specifically, the carbon monoxide partial pressure of the hydroformylation reaction in general may range from about 1 to about 3000 psia, and preferably from about 3 to about 1500 psia, while the hydrogen partial pressure in general may range from about 1 to about 3000 psia, and preferably from about 3 to about 1500 psia. In general, the molar ratio of carbon monoxide to gaseous hydrogen may range from about 100:1 or greater to about 1:100 or less, the preferred carbon monoxide to gaseous hydrogen molar ratio being from about 1:10 to about 10:1. The carbon monoxide and hydrogen partial pressures will be dependent in part on the particular catalyst system employed.

Carbon monoxide partial pressure should be sufficient for the hydroformylation reaction, e.g., of a pentenoic acid salt to a formylvaleric acid salt, to occur at an acceptable rate, but not so extreme that reaction rate and/or normal/branched aldehyde ratio may become unacceptably low. Hydrogen partial pressure must be sufficient for the hydroformylation reaction to occur at an acceptable rate, but not so high that hydrogenation of starting materials and intermediates, or isomerization of intermediates to undesired isomers, occurs. It is understood that carbon monoxide and hydrogen can be employed separately, in mixture with each other, i.e., synthesis gas, or may be produced in situ under reaction conditions.

Further, the hydroformylation process may be conducted at a reaction temperature from about 20° C. to about 200° C, preferably from about 50° C. to about 150° C, and more preferably from about 65° C to about 115° C. The temperature must be sufficient for reaction to occur (which may vary with catalyst system employed), but not so high that ligand or catalyst decomposition occurs. At high temperatures (which may vary with catalyst system employed), isomerization of intermediates to undesired isomers may occur.

Of course, it is to be also understood that the hydroformylation reaction conditions employed will be governed by the type of aldehyde salt product desired.

The hydroformylation reactions are also conducted in the presence of water or an organic solvent for the metal-ligand complex catalyst and free ligand. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of aldehyde acid salts, one may employ aldehyde acid compounds corresponding to the aldehyde acid salt products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehyde salts include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and glyme), 1,4-butanediols and sulfolane. Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

In an embodiment of the invention, the hydroformylation reaction mixture may consist of one or more liquid phases, e.g. a polar and a nonpolar phase. The reaction can be conducted in a liquid phase from which the product and/or catalyst can be separated by extraction into a separate liquid phase. A product-containing phase may also spontaneously separate during or after the reaction. Such processes are often advantageous in, for example, separating products from catalyst and/or reactants by partitioning into either phase. In addition, product selectivities dependent upon solvent properties may be increased by carrying out the reaction in that solvent. A well-known application of this technology is the aqueous-phase hydroformylation of olefins employing sulfonated phosphine ligands for the rhodium catalyst. A process carried out in aqueous solvent is particularly advantageous for the preparation of aldehyde salts because the products may be separated from the catalyst by extraction into an organic solvent. Alternatively, aldehydes which tend to undergo self-condensation reactions, are expected to be stabilized in aqueous solution as the aldehyde hydrates.

As described herein, the phosphorus-containing ligand for the rhodium hydroformylation catalyst may contain any of a number of substituents, such as cationic or anionic substituents, which will render the catalyst soluble in a polar phase, e.g. water. Optionally, a phase-transfer catalyst may be added to the reaction mixture to facilitate transport of the catalyst, reactants, or products into the desired solvent phase. The structure of the ligand or the phase-transfer catalyst is not critical and will depend on the choice of conditions, reaction solvent, and desired products.

When the catalyst is present in a multiphasic system, the catalyst may be separated from the reactants and/or products by conventional methods such as extraction or decantation. The reaction mixture itself may consist of one or more phases; alternatively, the multiphasic system may be created at the end of the reaction by for example addition of a second solvent to separate the products from the catalyst. See, for example, U.S. Pat. No. 5,180,854, the disclosure of which is incorporated herein by reference.

In an embodiment of the process of this invention, an olefin can be hydroformylated along with a pentenoic acid salt using the above-described metal-ligand complex catalysts. In such cases, an aldehyde derivative of the olefin is also produced along with the formylvaleric acid salt.

Mixtures of different olefinic starting materials can be employed, if desired, in the hydroformylation reactions. More preferably the hydroformylation reactions are especially useful for the production of formylvaleric acid salts, by hydroformylating pentenoic acid salts in the presence of alpha olefins containing from 2 to 30, preferably 4 to 20, carbon atoms, including isobutylene, and internal olefins containing from 4 to 20 carbon atoms as well as starting material mixtures of such alpha olefins and internal olefins. Commercial alpha olefins containing four or more carbon atoms may contain minor amounts of corresponding internal olefins and/or their corresponding saturated hydrocarbon and that such commercial olefins need not necessarily be purified from same prior to being hydroformylated.

Illustrative of other olefinic starting materials include alpha-olefins, internal olefins, 1,3-dienes, alkyl alkenoates, alkenyl alkanoates, alkenyl alkyl ethers, alkenols, alkenals, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, piperylene, isoprene, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, vinyl cyclohexene, allyl ethyl ether, methyl pentenoate, 3-pentenoic acid, n-propyl-7-octenoate, pentenals, e.g., 2-pentenal, 3-pentenal and 4-pentenal; pentenols, e.g., 2-pentenol, 3-pentenol and 4-pentenol; 3-butenenitrile, 3-pentenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, 4-allylanisole, indene, limonene, beta-pinene, dicyclopentadiene, cyclooctadiene, camphene, linalool, and the like. Other illustrative olefinic compounds may include, for example, p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described in U.S. Pat. No. 4,329,507, the disclosure of which is incorporated herein by reference.

As indicated above, it is generally preferred to carry out the hydroformylation process of this invention in a continuous manner. In general, continuous hydroformylation processes are well known in the art and may involve: (a) hydroformylating the olefinic salt starting material(s) with carbon monoxide and hydrogen in a liquid homogeneous reaction mixture comprising a solvent, the metal-ligand complex catalyst, and free ligand; (b) maintaining reaction temperature and pressure conditions favorable to the hydroformylation of the olefinic salt starting material(s); (c) supplying make-up quantities of the olefinic salt starting material(s), carbon monoxide and hydrogen to the reaction medium as those reactants are used up; and (d) recovering the desired aldehyde salt hydroformylation product(s) in any manner desired. The continuous process can be carried out in a single pass mode, i.e., wherein the aldehyde acid salt product is removed from the liquid reaction mixture from whence a product is recovered and make-up olefinic salt starting material(s), carbon monoxide and hydrogen are supplied to the liquid reaction medium for the next single pass through without recycling the unreacted olefinic salt starting material(s). However, it is generally desirable to employ a continuous process that involves either a liquid and/or gas recycle procedure. Such types of recycle procedure are well known in the art and may involve the liquid recycling of the metal-ligand complex catalyst solution separated from the desired aldehyde reaction product(s), such as disclosed e.g., in U.S. Pat. No. 4,148,830 or a gas cycle procedure such as disclosed e.g., in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process.

Illustrative substituted and unsubstituted aldehyde acid salt intermediates that can be prepared by the processes of this invention include substituted and unsubstituted formylcarboxylic acid salts such as 5-formylvaleric acid salts and the like, e.g., triethylammonium 5-formylvalerate, ammonium 5-formylvalerate and octyltriethylammonium 5-formylvalerate. Illustrative of suitable substituted and unsubstituted aldehyde acid salts (including derivatives of substituted and unsubstituted aldehyde acid salts) include those permissible substituted and unsubstituted aldehyde acid salts which may be described in Kirk-Othmer, Encyclopedia of Chemical Technology, Fourth Edition, 1996, the pertinent portions of which are incorporated herein by reference.

Illustrative substituted and unsubstituted epsilon caprolactam precursors that can be prepared by the processes of this invention include one or more substituted and unsubstituted 5-formylvaleric acid salts, iminocaproic acid and/or salts thereof, aminocaproic acid and/or salts thereof, caprolactam, caprolactone, imines, hemiaminals, imides, amides or amines derived from formylvaleric acid and its salts, and the corresponding dimers, trimers and oligomers. Illustrative of suitable substituted and unsubstituted epsilon caprolactam precursors (including derivatives of substituted and unsubstituted epsilon caprolactam precursors) include those permissible substituted and unsubstituted epsilon caprolactam precursors which may be described in Kirk-Othmer, Encyclopedia of Chemical Technology, Fourth Edition, 1996, the pertinent portions of which are incorporated herein by reference.

In an embodiment of this invention, the aldehyde salt mixtures may be separated from the other components of the crude reaction mixtures in which the aldehyde salt mixtures are produced by any suitable method. Suitable separation methods include, for example, solvent extraction, crystallization, distillation, vaporization, phase separation, sublimation, wiped film evaporation, falling film evaporation and the like. It may be desired to remove the aldehyde products from the crude reaction mixture as they are formed through the use of trapping agents as described in published Patent Cooperation Treaty Patent Application WO 88/08835. A method for separating the aldehyde salt mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, both incorporated herein by reference. The subsequent reductive cyclization or amination and cyclization of the aldehyde salt mixtures may be conducted without the need to separate the aldehyde salts from the other components of the crude reaction mixtures.

A process for producing one or more substituted or unsubstituted aldehyde acid salts from one or more substituted or unsubstituted unsaturated acid salts is disclosed in copending U.S. patent application Ser. No. (D-17765), filed on an even date herewith, the disclosure of which is incorporated herein by reference.

Particularly when conducting the process of this invention in a continuous liquid recycle mode employing an organophosphite ligand, undesirable acidic byproducts (e.g., a hydroxy alkyl phosphonic acid) may result due to reaction of the organophosphite ligand and the aldehyde over the course of the process. The formation of such byproducts undesirably lowers the concentration of the ligand. Such acids are often insoluble in the reaction mixture and such insolubility can lead to precipitation of an undesirable gelatinous byproduct and may also promote the autocatalytic formation of further acidic byproducts. The organopolyphosphite ligands used in the process of this invention have good stability against the formation of such acids. However, if this problem does occur, the liquid reaction effluent stream of a continuous liquid recycle process may be passed, prior to (or more preferably after) separation of the desired 5-formylvaleric acid salt product therefrom, through any suitable weakly basic anion exchange resin, such as a bed of amine Amberlyst® resin, e.g., Amberlyst® A-21, and the like, to remove some or all of the undesirable acidic byproducts prior to its reincorporation into the hydroformylation reactor. If desired, more than one such basic anion exchange resin bed, e.g. a series of such beds, may be employed and any such bed may be easily removed and/or replaced as required or desired. Alternatively if desired, any part or all of the acid-contaminated catalyst recycle stream may be periodically removed from the continuous recycle operation and the contaminated liquid so removed treated in the same fashion as outlined above, to eliminate or reduce the amount of acidic by-product prior to reusing the catalyst containing liquid in the hydroformylation process. Likewise, any other suitable method for removing such acidic byproducts from the hydroformylation process of this invention may be employed herein if desired such as by extraction of the acid with a weak base (e.g., sodium bicarbonate).

The processes useful in this invention may involve improving the catalyst stability of any organic solubilized rhodium-organopolyphosphite complex catalyzed, liquid recycle hydroformylation process directed to producing aldehydes from olefinic unsaturated compounds which may experience deactivation of the catalyst due to recovery of the aldehyde product by vaporization separation from a reaction product solution containing the organic solubilized rhodium-organopolyphosphite complex catalyst and aldehyde product, the improvement comprising carrying out said vaporization separation in the presence of a heterocyclic nitrogen compound. See, for example, copending U.S. patent application Ser. No. 08/756,789, filed Nov. 26, 1996, the disclosure of which is incorporated herein by reference.

The processes useful in this invention may involve improving the hydrolytic stability of the organophosphite ligand and thus catalyst stability of any organic solubilized rhodium-organophosphite ligand complex catalyzed hydroformylation process directed to producing aldehydes from olefinic unsaturated compounds, the improvement comprising treating at least a portion of an organic solubilized rhodium-organophosphite ligand complex catalyst solution derived from said process and which also contains phosphorus acidic compounds formed during the hydroformylation process, prior to (or more preferably after) separation of the desired 5-formylvaleric acid salt product therefrom, with an aqueous buffer solution in order to neutralize and remove at least some amount of said phosphorus acidic compounds from said catalyst solution, and then returning the treated catalyst solution to the hydroformylation reactor. See, for example, copending U.S. patent application Ser. Nos. 08/756,501 and 08/753,505, both filed Nov. 26, 1996, the disclosures of which are incorporated herein by reference.

In an embodiment of this invention, deactivation of metal-organopolyphosphorus ligand complex catalysts caused by an inhibiting or poisoning organomonophosphorus compound can be reversed or at least minimized by carrying out hydroformylation processes in a reaction region where the hydroformylation reaction rate is of a negative or inverse order in carbon monoxide and optionally at one or more of the following conditions: at a temperature such that the temperature difference between reaction product fluid temperature and inlet coolant temperature is sufficient to prevent and/or lessen cycling of carbon monoxide partial pressure, hydrogen partial pressure, total reaction pressure, hydroformylation reaction rate and/or temperature during said hydroformylation process; at a carbon monoxide conversion sufficient to prevent and/or lessen cycling of carbon monoxide partial pressure, hydrogen partial pressure, total reaction pressure, hydroformylation reaction rate and/or temperature during said hydroformylation process; at a hydrogen conversion sufficient to prevent and/or lessen cycling of carbon monoxide partial pressure, hydrogen partial pressure, total reaction pressure, hydroformylation reaction rate and/or temperature during said hydroformylation process; and at an olefinic unsaturated compound conversion sufficient to prevent and/or lessen cycling of carbon monoxide partial pressure, hydrogen partial pressure, total reaction pressure, hydroformylation reaction rate and/or temperature during said hydroformylation process. See, for example, copending U.S. patent application Ser. No. 08/756, 499, filed Nov. 26, 1996, the disclosure of which is incorporated herein by reference.

A preferred embodiment of this invention for producing one or more substituted or unsubstituted epsilon caprolactams involves a process which comprises:

(a) subjecting one or more substituted or unsubstituted alkadienes, e.g., butadiene, to hydroxycarbonylation in the presence of a hydroxycarbonylation catalyst, e.g., a metal-organophosphorus ligand complex catalyst, to produce one or more substituted or unsubstituted unsaturated acids, e.g., pentenoic acids comprising cis-3-pentenoic acids, trans-3-pentenoic acids, 4-pentenoic acid, cis-2-pentenoic acids and/or trans-2-pentenoic acids;

(b) optionally separating the unsaturated acids from the hydroxycarbonylation catalyst;

(c) subjecting the unsaturated acids to neutralization to produce one or more substituted or unsubstituted pentenoic acid salts, e.g., cis-3-pentenoic acid salts, trans-3-pentenoic acid salts, 4-pentenoic acid salt, cis-2-pentenoic acid salts and/or trans-2-pentenoic acid salts;

(d) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., 5-formylvaleric acid salt, and/or one or more substituted or unsubstituted epsilon caprolactam precursors;

(e) optionally separating the formylvaleric acid salts from the hydroformylation catalyst; and (f) subjecting said one or more substituted or unsubstituted formylvaleric acid salts and/or said one or more substituted or unsubstituted epsilon caprolactam precursors to reductive cyclization in the presence of a reductive cyclization catalyst or to amination optionally in the presence of an amination catalyst and cyclization in the presence of a cyclization catalyst to produce said one or more substituted or unsubstituted epsilon caprolactams, e.g., epsilon caprolactam.

Yet another preferred embodiment of this invention for producing one or more substituted or unsubstituted epsilon caprolactams involves a process which comprises:

(a) subjecting one or more substituted or unsubstituted alkadienes, e.g., butadiene, to hydroxycarbonylation in the presence of a hydroxycarbonylation catalyst, e.g., a metal-organophosphorus ligand complex catalyst, to produce one or more substituted or unsubstituted unsaturated acids, e.g., pentenoic acids comprising cis-3-pentenoic acids, trans-3-pentenoic acids, 4-pentenoic acid, cis-2-pentenoic acids and/or trans-2-pentenoic acids;

(b) optionally separating the unsaturated acids from the hydroxycarbonylation catalyst;

(c) optionally subjecting the unsaturated acids to isomerization in the presence of a heterogeneous or homogeneous olefin isomerization catalyst to partially or completely isomerize the 2-pentenoic acids and/or 3-pentenoic acids to 3-pentenoic acids and/or 4-pentenoic acid;

(d) subjecting the unsaturated acids to neutralization to produce one or more substituted or unsubstituted pentenoic acid salts, e.g., cis-3-pentenoic acid salts, trans-3-pentenoic acid salts, 4-pentenoic acid salt, cis-2-pentenoic acid salts and/or trans-2-pentenoic acid salts;

(e) subjecting said one or more substituted or unsubstituted pentenoic acid salts to hydroformylation in the presence of a hydroformylation catalyst, e.g., a metal-organophosphorus ligand complex catalyst, to produce one or more substituted or unsubstituted formylvaleric acid salts, e.g., 5-formylvaleric acid salt, and/or one or more substituted or unsubstituted epsilon caprolactam precursors;

(f) optionally separating the formylvaleric acid salts from the hydroformylation catalyst; and (g) subjecting said one or more substituted or unsubstituted formylvaleric acid salts and/or said one or more substituted or unsubstituted epsilon caprolactam precursors to reductive cyclization in the presence of a reductive cyclization catalyst or to reductive amination in the presence of a reductive amination catalyst and cyclization optionally in the presence of a cyclization catalyst to produce said one or more substituted or unsubstituted epsilon caprolactams, e.g., epsilon caprolactam. In an embodiment, step (d) may optionally include subjecting the unsaturated acid salts to isomerization in the presence of a heterogeneous or homogeneous olefin isomerization catalyst to partially or completely isomerize the 2-pentenoic acid salts and/or 3-pentenoic acid salts to 3-pentenoic acid salts and/or 4-pentenoic acid salt.

The olefin isomerization catalyst in step (c) may be any of a variety of homogeneous or heterogeneous transition metal-based catalysts (particularly Ni, Rh, Pd, Pt, Co, Ru, or Ir), or may be a heterogeneous or homogeneous acid catalyst (particularly any acidic zeolite, polymeric resin, or source of $H^+$, any of which may be modified with one or more transition metals). Such olefin isomerization catalysts are known in the art and the isomerization can be conducted by conventional procedures known in the art. As used herein, the term "isomerization" is contemplated to include, but is not limited to, all permissible isomerization processes which involve converting one or more substituted or unsubstituted 2-pentenoic acids and/or 3-pentenoic acids to substituted or unsubstituted 4-pentenoic acid.

When the processes for producing a formylvaleric acid salt are conducted in three stages (i.e., first producing 2-pentenoic acids, 3-pentenoic acids and/or 4-pentenoic acid under one set of conditions and then producing a pentenoic acid salt from the 2-pentenoic acids, 3-pentenoic acids and/or 4-pentenoic acid under another set of conditions and then producing a 5-formylvaleric acid salt under another set of conditions), it is preferred to conduct the first and third stages at a temperature from 75° C. to 110° C. and at a total pressure from 250 psi to 1000 psi and to conduct the second stage at a temperature from 60° C. to 100° C. and at a pressure from 100 psi to 500 psi. The same or different metal-ligand complex catalyst can be used in the first and third stages. The other conditions can be the same or different in both stages.

Reductive Cyclization Step

The reductive cyclization process involves converting one or more substituted or unsubstituted formylvaleric acid salts, e.g., 5-formylvaleric acid salt, and/or one or more substituted or unsubstituted epsilon caprolactam precursors to one or more substituted or unsubstituted epsilon caprolactams in one or more steps or stages. As used herein, the term "reductive cyclization" is contemplated to include all permissible reductive cyclization processes which involve hydrogenation and cyclization for converting one or more substituted or unsubstituted formylvaleric acid salts, e.g., 5-formylvaleric acid salt, and/or one or more substituted or unsubstituted epsilon caprolactam precursors to one or more substituted or unsubstituted epsilon caprolactams. As used herein, the term "hydrogenation" is contemplated to include all permissible hydrogenation processes which in conjunction with cyclization involve converting one or more substituted or unsubstituted formylvaleric acid salts, e.g., 5-formylvaleric acid salt, and/or one or more substituted or unsubstituted epsilon caprolactam precursors to one or more substituted or unsubstituted epsilon caprolactams. As used herein, the term "cyclization" is contemplated to include all permissible cyclization processes which in conjunction with hydrogenation involve converting one or more substituted or unsubstituted formylvaleric acid salts, e.g., 5-formylvaleric acid salt, and/or one or more substituted or unsubstituted epsilon caprolactam precursors to one or more substituted or unsubstituted epsilon caprolactams. In general, the reductive cyclization step or stage comprises reacting one or more substituted or unsubstituted aldehyde acid salts and/or one or more substituted or unsubstituted epsilon caprolactam precursors with hydrogen in the presence of a catalyst to produce one or more substituted or unsubstituted epsilon caprolactams.

Formylvaleric acid salts and/or epsilon caprolactam precursors useful in the reductive cyclization process are known materials and can be prepared by the hydroformylation steps described above or by other conventional processes. Reaction mixtures comprising formylvaleric acid salts and/or epsilon caprolactam precursors may be useful herein. The amounts of formylvaleric acid salts and/or epsilon caprolactam precursors employed in the reductive cyclization step is not narrowly critical and can be any amounts sufficient to produce epsilon caprolactam, preferably in high selectivities.

The reductive cyclization process may be carried out in one or more steps or stages and in any permissible sequence of steps or stages. In a one step process, epsilon caprolactam is the desired product leaving the reaction zone. In a multistep or multistage process, intermediate products are the major products leaving the individual reaction zones.

The particular reductive cyclization reaction conditions are not narrowly critical and can be any effective hydrogenation and cyclization conditions sufficient to produce the epsilon caprolactams. The reactors may be stirred tanks, tubular reactors and the like. The exact reaction conditions will be governed by the best compromise between achieving high catalyst selectivity, activity, lifetime and ease of operability, as well as the intrinsic reactivity of the formylvaleric acid salts and/or epsilon caprolactam precursors in question and the stability of the formylvaleric acid salts and/or epsilon caprolactam precursors and the desired reaction product to the reaction conditions. Illustrative of certain reaction conditions that may be employed in the hydrogenation and/or cyclization processes are described, for example, in U.S. Pat. Nos. 3,652,549 and 4,730,041, the disclosures of which are incorporated herein by reference. Products may be recovered after a particular reaction zone and purified if desired although they may be introduced to the next reaction zone without purification. Recovery and purification may be by any appropriate means, which will largely be determined by the particular epsilon caprolactam precursor employed, and may include distillation, phase separation, extraction, absorption, crystallization, derivative formation and the like.

While not wishing to be bound by any particular theory, the hydrogenation of an epsilon caprolactam precursor, e.g., 5-formylvaleric acid salt, and cyclization to epsilon caprolactam may proceed through a variety of intermediates. The catalysts which are best able to promote the selectivity or rate of such a transformation will depend on the particular mechanism followed. Catalysts capable of catalyzing hydrogenation or dehydrogenation reactions are desirably used.

The hydrogenation may be carried out using a variety of known catalysts in conventional amounts. Such catalysts comprise a variety of materials, including homogeneous and heterogeneous catalysts, such as palladium, ruthenium, platinum, rhodium, copper chromite, nickel, copper, cobalt, and the like. These metal catalysts can be supported on a variety of supports, including titania, magnesium silicate, alumina, vanadia and the like, and may be further promoted by additional metals or other additives, for example, barium, manganese, zirconium, selenium, calcium, molybdenum, cobalt, and the like. Other illustrative catalysts comprise a variety of materials, including homogeneous and heterogeneous catalysts, or other Group 8, 9 and 10 metals, copper, chromium oxide, and a variety of metal nitrides and carbides, and the like. These metal catalysts can be supported on a variety of supports, including titania, lanthanum oxide, ceria, silicon carbide, magnesium silicate, aluminas, silica-aluminas, vanadia and the like, and may be further promoted by additional metals or other additives, for example, barium, manganese, zirconium, selenium, calcium, molybdenum, cobalt or other Group 8, 9 and 10 metals, copper, iron, and zinc. A variety of homogeneous catalysts may also be employed, for example rhodium, ruthenium, cobalt, nickel and the like. Such catalysts can be promoted or stabilized by a variety of ligands including nitrogen or phosphorus containing materials such amines, phosphines, phosphites and similar materials.

The hydrogenation reaction may be carried out in any desired manner, for example in a tubular or a stirred tank reactor, and the like. The hydrogenation reaction can be carried out by conventional methods. For example, reaction temperatures may range from about 50° C. to about 400° C. or higher, preferably from about 100° C. to about 300° C. for a period of about 1 hour or less to about 4 hours or longer with the longer time being used at the lower temperature. Reaction pressures may range from atmospheric or subatmospheric to about 3000 psi or greater. Preferably, mild temperatures and low pressures are generally considered desirable, consistent with acceptable catalyst performance and lifetime, and epsilon caprolactam precursor and epsilon caprolactam product stability. The amount of hydrogenation catalyst used is dependent on the particular hydrogenation catalyst employed and can range from about 0.01 weight percent or less to about 10 weight percent or greater of the total weight of the starting materials.

The cyclization reaction of an epsilon caprolactam precursor in which at least one functionality is a nitrogen containing functional group such as amine may or may not need a catalyst, depending on the particular epsilon caprolactam precursor employed. Although it may not be absolutely necessary to employ a catalyst, it still may be desirable to do so to improve the selectivity or rate of the transformation. Other epsilon caprolactam precursors may necessitate the use of an appropriate catalyst. Since the mechanism of the cyclization reaction depends on the epsilon caprolactam precursor, the useful catalysts will be selected based upon the epsilon caprolactam precursor employed.

The cyclization reaction may be performed in any appropriate solvent, such as water, aromatic or aliphatic hydrocarbons or functionalized solvents such as methanol, ethanol, ketones and the like, or may be carried out using the pure epsilon caprolactam precursor or the epsilon caprolactam precursor and a mixture of byproducts from the earlier stages of the reaction sequence. If the transformation is carried out in the presence of water, it is desirable that the solvent mixture employed be capable of dissolving all components of the reaction mixture, except any heterogeneous catalysts that may be employed.

A two phase system may also be used, providing adequate mixing is achieved. Such a system, however, may be used to facilitate recovery of epsilon caprolactam after the cyclization reaction by extraction, phase separation or crystallization. Cyclization reaction conditions may range from about 0° C. to about 400° C. and subatmospheric to about 3000 psi or greater for a period of about 1 hour or less to about 4 hours or longer with the longer time being used at the lower temperature, more preferably from about 50° C. to about 350° C. and from about 50 psi to about 2500 psi. The amount of catalyst used, if any, is dependent on the particular catalyst employed and can range from about 0.01 weight percent or less to about 10 weight percent or greater of the total weight of the starting materials. It may be desirable to combine hydrogenation and cyclization steps into a single reaction zone.

As indicated above, the substituted and unsubstituted epsilon caprolactams produced by the reductive cyclization step of this invention can be separated by conventional techniques such as distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the hydrogenation and cyclization reaction step.

Reductive Amination and Cyclization Step(s)

The reductive amination and cyclization process involves converting one or more substituted or unsubstituted formylvaleric acid salts, e.g., 5-formylvaleric acid salt, and/or one or more substituted or unsubstituted epsilon caprolactam precursors to one or more substituted or unsubstituted epsilon caprolactams in one or more steps or stages. As used herein, the term "cyclization" is contemplated to include all permissible cyclization processes which in conjunction with amination involve converting one or more substituted or unsubstituted formylvaleric acid salts, e.g., 5-formylvaleric acid salt, and/or one or more substituted or unsubstituted epsilon caprolactam precursors to one or more substituted or unsubstituted epsilon caprolactams. As used herein, the term "reductive amination" is contemplated to include all permissible reductive amination processes which in conjunction with cyclization involve converting one or more substituted or unsubstituted formylvaleric acid salts, e.g., 5-formylvaleric acid salt, and/or one or more substituted or unsubstituted epsilon caprolactam precursors to one or more substituted or unsubstituted epsilon caprolactams. In general, the reductive amination and cyclization steps or stages comprise reacting one or more substituted or unsubstituted aldehyde acid salts and/or one or more substituted or unsubstituted epsilon caprolactam precursors with hydrogen and an amine or ammonia in the presence of a catalyst to produce one or more substituted or unsubstituted epsilon caprolactams.

Illustrative substituted and unsubstituted formylvaleric acid salts include, for example, 5-formylvaleric acid salts such as triethylammonium 5-formylvalerate, ammonium 5-formylvalerate, or their oligomers and their hydrates or oligomers, and the like. Formylvaleric acid salts and/or epsilon caprolactam precursors useful in the reductive amination and cyclization process are known materials and can be prepared by the hydroformylation steps described above or by other conventional processes. Reaction mixtures comprising formylvaleric acid salts and/or epsilon caprolactam precursors may be useful herein. The amounts of formylvaleric acid salts and/or epsilon caprolactam precursors employed in the reductive amination and cyclization step is not narrowly critical and can be any amounts sufficient to produce epsilon caprolactam, preferably in high selectivities.

The reductive amination and cyclization process may be carried out in one or more steps or stages and in any permissible sequence of steps or stages. In a one step process, epsilon caprolactam is the desired product leaving the reaction zone. In a multistep or multistage process, intermediate products are the major products leaving the individual reaction zones. For example, in a three stage process, an epsilon caprolactam precursor, e.g., 5-formylvaleric acid salt, may be converted to an imine in a first stage, the imine may be hydrogenated to an amine in a second stage, e.g., 6-aminocaproic acid or salts thereof, and the amine may be cyclized to epsilon caprolactam in a third stage. In a two stage process, an epsilon caprolactam precursor, e.g., 5-formylvaleric acid salt, may be converted directly to an amine, e.g., 6-aminocaproic acid or salts thereof, in a first stage, and the amine may be cyclized to epsilon caprolactam in a second stage. Of course some overlap of these individual transformations may occur, so that in a two stage process, some cyclization may occur in the first stage.

The particular amination and cyclization reaction conditions are not narrowly critical and can be any effective amination and cyclization conditions sufficient to produce the epsilon caprolactam. The reactors may be stirred tanks, tubular reactors and the like. The exact reaction conditions will be governed by the best compromise between achieving high catalyst selectivity, activity, lifetime and ease of operability, as well as the intrinsic reactivity of the formylvaleric acid salts and/or epsilon caprolactam precursors in question and the stability of the formylvaleric acid salts and/or epsilon caprolactam precursors and the desired reaction product to the reaction conditions. Illustrative of certain reaction conditions that may be employed in the reductive amination and/or cyclization processes are described, for example, in U.S. Pat. Nos. 4,730,840, 4,730,841, 4,731,445 and 5,068,398, the disclosures of which are incorporated herein by reference. Products may be recovered after a particular reaction zone and purified if desired although they may be introduced to the next reaction zone without purification. Recovery and purification may be by any appropriate means, which will largely be determined by the particular epsilon caprolactam precursor employed, and may include distillation, phase separation, extraction, absorption, crystallization, derivative formation and the like.

The reductive amination reaction can be conducted at a temperature of from about 0° C. to about 200° C. for a period of about 1 hour or less to about 4 hours or longer with the longer time being used at the lower temperature, preferably from about 10° C. to about 150° C. for about 1 hour or less to about 2 hours or longer, and more preferably at about 20° C. to about 125° C. for about 1 hour or less. The temperature should be sufficient for reaction to occur (which may vary with catalyst system) but not so high as to cause 5-formylvaleric acid salt decomposition or polymerization.

The reductive amination reaction can be conducted over a wide range of pressures ranging from about 20 psig to about 2000 psig. It is preferable to conduct the reductive amination reaction at pressures of from about 100 psig to about 1000 psig. The reductive amination reaction is preferably effected in the liquid or vapor states or mixtures thereof. The total pressure will depend on the catalyst system used. Hydrogen partial pressure can be chosen to maximize the lifetime of the hydrogenation catalyst.

Ammonia is preferably employed as the aminating agent in these reactions in conventional amounts, preferably in excess amounts, and it may be fed to the reactor in a variety of ways, including as a liquid, and a gas, in solution in for example water, or as ammonium salts in solution or in some other appropriate manner. Any excess ammonia is preferably separated off after amination is completed. The formylvaleric acid salts and/or epsilon caprolactam precursors may be fed to the reactor in any convenient manner, such as in solution, or as a neat liquid.

Some of the reaction steps or stages may involve the use of a catalyst. Such catalysts are known in the art and can be used in conventional amounts. For example, the hydrogenation of an imine to an amine may advantageously employ an appropriate hydrogenation catalyst.

Catalysts suitable for possible intermediate imination reactions, e.g., conversion of an aldehyde to an imine, include mild acids, for example mineral acids, and carboxylic acids, such as hydrochloric acid, phosphoric acid, sulfuric acid, acetic acid benzoic acid, and the like. Other acidic materials may also be used, such as molecular sieves, silicas, aluminas and aluminosilicas, clays, and hydrous titanates. Heteropolyacids, sulfonic acids, phenols or other mildly acidic materials may also be used.

It may also be advantageous to remove the water produced in an intermediate imination reaction by, for example, azeotropic distillation, extraction, absorption and other like means. Alternatively, and depending on the particular epsilon caprolactam precursor employed, the water may not be intentionally removed, but be carried through to the next stage of the reaction.

While not wishing to be bound by any particular theory, the reductive amination of an epsilon caprolactam precursor, e.g., 5-formylvaleric acid salt, and cyclization to epsilon caprolactam may proceed through a variety of intermediates. The catalysts which are best able to promote the selectivity or rate of such a transformation will depend on the particular mechanism followed. Catalysts capable of catalyzing hydrogenation or dehydrogenation reactions are desirably used.

A further transformation in the reaction sequence is the reduction of imine to amine functionality, i.e., hydrogenation reaction. This transformation may be carried out using a variety of known catalysts, such as hydrogenation or dehydrogenation catalysts, in conventional amounts. Such catalysts comprise a variety of materials, including homogeneous and heterogeneous catalysts, such as palladium, ruthenium, platinum, rhodium, copper chromite, nickel, copper, cobalt, and the like. These metal catalysts can be supported on a variety of supports, including titania, magnesium silicate, alumina, vanadia and the like, and may be further promoted by additional metals or other additives, for example, barium, manganese, zirconium, selenium, calcium, molybdenum, cobalt, and the like. Other illustrative catalysts comprise a variety of materials, including homogeneous and heterogeneous catalysts, or other Group 8, 9 and 10 metals, copper, chromium oxide, and a variety of metal nitrides and carbides, and the like. These metal catalysts can be supported on a variety of supports, including titania, lanthanum oxide, ceria, silicon carbide, magnesium silicate, aluminas, silica-aluminas, vanadia and the like, and may be further promoted by additional metals or other additives, for example, barium, manganese, zirconium, selenium, calcium, molybdenum, cobalt or other Group 8, 9 and 10 metals, copper, iron, and zinc. A variety of homogeneous catalysts may also be employed, for example rhodium, ruthenium, cobalt, nickel and the like. Such catalysts can be promoted or stabilized by a variety of ligands including nitrogen or phosphorus containing materials such amines, phosphines, phosphites and similar materials.

The hydrogenation reaction may be carried out in any desired manner, for example in a tubular or a stirred tank reactor, and the like. The hydrogenation reaction can be carried out by conventional methods. For example, reaction temperatures may range from about 50° C. to about 400° C. or higher, preferably from about 100° C. to about 300° C. for a period of about 1 hour or less to about 4 hours or longer with the longer time being used at the lower temperature. Reaction pressures may range from atmospheric or subatmospheric to about 3000 psi or greater. Preferably, mild temperatures and low pressures are generally considered desirable, consistent with acceptable catalyst performance and lifetime, and epsilon caprolactam precursor and epsilon caprolactam product stability. The amount of hydrogenation catalyst used is dependent on the particular hydrogenation catalyst employed and can range from about 0.01 weight percent or less to about 10 weight percent or greater of the total weight of the starting materials.

The cyclization reaction of an epsilon caprolactam precursor in which at least one functionality is a nitrogen containing functional group such as amine or imine may or may not need a catalyst, depending on the particular epsilon caprolactam precursor employed. Although it may not be absolutely necessary to employ a catalyst, it still may be desirable to do so to improve the selectivity or rate of the transformation. Other epsilon caprolactam precursors may necessitate the use of an appropriate catalyst. Since the mechanism of the cyclization reaction depends on the epsilon caprolactam precursor, the useful catalysts will be selected based upon the epsilon caprolactam precursor employed.

The cyclization reaction may be performed in any appropriate solvent, such as water, aromatic or aliphatic hydrocarbons or functionalized solvents such as methanol, ethanol, ketones and the like, or may be carried out using the pure epsilon caprolactam precursor or the epsilon caprolactam precursor and a mixture of byproducts from the earlier stages of the reaction sequence. If the transformation is carried out in the presence of water, it is desirable that the solvent mixture employed be capable of dissolving all components of the reaction mixture, except any heterogeneous catalysts that may be employed.

A two phase system may also be used, providing adequate mixing is achieved. Such a system, however, may be used to facilitate recovery of epsilon caprolactam after the cyclization reaction by extraction, phase separation or crystallization. Cyclization reaction conditions may range from about 0° C. to about 400° C. and subatmospheric to about 3000 psi or greater for a period of about 1 hour or less to about 4 hours or longer with the longer time being used at the lower temperature, more preferably from about 50° C. to about 350° C. and from about 50 psi to about 2500 psi. The amount of catalyst used, if any, is dependent on the particular catalyst employed and can range from about 0.01 weight percent or less to about 10 weight percent or greater of the total weight of the starting materials. It may be desirable to combine amination and cyclization steps into a single reaction zone.

As indicated above, the substituted and unsubstituted epsilon caprolactams produced by the reductive amination and cyclization step of this invention can be separated by conventional techniques such as distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the reductive amination and cyclization reaction step.

Illustrative epsilon caprolactams that can be prepared by the processes of this invention include epsilon caprolactam and substituted epsilon caprolactams (e.g., alpha, beta, gamma, delta and N-substituted epsilon caprolactams). Illustrative of suitable substituted and unsubstituted epsilon caprolactams (including derivatives of epsilon caprolactams) include those permissible substituted and unsubstituted epsilon caprolactams which are described in Kirk-Othmer, Encyclopedia of Chemical Technology, Fourth Edition, 1996, the pertinent portions of which are incorporated herein by reference.

The epsilon caprolactams described herein are useful in a variety of applications, such as the manufacture of synthetic fibers (especially nylon 6), plastics, bristles, film, coatings, synthetic leather, plasticizers and paint vehicles, crosslinking agent for polyurethanes, synthesis of amino acid lysine and the like.

The processes of this invention can be operated over a wide range of reaction rates (m/L/h=moles of product/liter of reaction solution/hour). Typically, the reaction rates are at least 0.01 m/L/h or higher, preferably at least 0.1 m/L/h or higher, and more preferably at least 0.5 m/L/h or higher. Higher reaction rates are generally preferred from an economic standpoint, e.g., smaller reactor size, etc.

A process for producing one or more substituted or unsubstituted epsilon caprolactams from one or more substituted or unsubstituted alkadienes is disclosed in copending U.S. patent application Ser. No. 60/016,126, filed Apr. 24, 1996, the disclosure of which is incorporated herein by reference.

The processes of this invention may be carried out using, for example, a fixed bed reactor, a fluid bed reactor, or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more steps or stages. For example, in a one stage process, 5-formylvalerate may be hydrogenated in the first part of a tubular reactor and cyclized in the latter part of the tubular reactor. The exact number of reaction steps or stages will be governed by the best compromise between achieving high catalyst selectivity, activity, lifetime and ease of operability, as well as the intrinsic reactivity of the starting materials in question and the stability of the starting materials and the desired reaction product to the reaction conditions.

In an embodiment, the processes useful in this invention may be carried out in a multistaged reactor such as described, for example, in copending U.S. patent application Ser. No.08/757,743, filed on Nov. 26, 1996, the disclosure of which is incorporated herein by reference. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

The substituted and unsubstituted epsilon caprolactams produced by the processes of this invention can undergo further reaction(s) to afford desired derivatives thereof. Such permissible derivatization reactions can be carried out in accordance with conventional procedures known in the art. Illustrative derivatization reactions include, for example, hydrogenation, esterification, polymerization, copolymerization, amination, alkylation, dehydrogenation, reduction, acylation, condensation, oxidation, silylation and the like, including permissible combinations thereof. This invention is not intended to be limited in any manner by the permissible derivatization reactions or permissible derivatives of substituted and unsubstituted epsilon caprolactams.

In an embodiment of this invention, after optional purification of epsilon caprolactam, nylon 6 polymer is produced from epsilon caprolactam by continuous polymerization or batch polymerization processes. In both reaction processes for forming nylon 6, polymerization occurs according to the following reactions: epsilon caprolactam (mol. wt. 113)+ $H_2O \rightarrow$ aminocaproic acid (mol. wt. 131) $\rightarrow$ nylon 6 (mol. wt. 14,000–20,000)+$H_2O$. Suitable reactors and polymerization reaction conditions for nylon 6 are known in the art.

In a continuous polymerization process, high-purity, molten caprolactam is taken from storage and pumped to a tank where controlled amounts of water (the initiator), recovered monomer and oligomers, a chain terminator (e.g., acetic acid) and other additives such as heat and light stabilizers are mixed together. The caprolactam is maintained in a nitrogen environment both in the holding tanks and throughout the polymerization process. The melted caprolactam solution is then filtered and metered into the reaction vessel where polymerization occurs.

The reaction vessel, which is generally eight to ten meters high and mounted vertically, is usually equipped with several independent heating jackets that control the temperature of the reactants as they pass down the tube. Polymerization occurs at atmospheric pressure as the reactants pass slowly through the tube and as the temperature increases to about 275° C. After 20–24 hours, the nylon 6 polymer reaches equilibrium and is extruded as strands into a water quenching bath; the strands are then cut into chips that are also stored under nitrogen.

In a batch polymerization process, high-purity melted epsilon caprolactam (about 80° C.) is pumped into an autoclave. Water, which serves as an initiator, is added to form up to a 5% solution and the temperature of the solution is increased to 220–270° C. The pressure increases with increasing temperature, and polymerization occurs.

Addition of a polymer chain terminator such as acetic acid controls molecular weight and thus the viscosity of the resin. After several hours, when the caprolactam conversion to polymer has reached equilibrium, water is removed by reducing the pressure to achieve a vacuum. The removal of water is necessary to achieve the desired molecular weight. After the water removal, the polymerization mixture may be held until the molecular weight reaches equilibrium. Finally, the molten resin is extruded as strands into a water quenching bath; the strands are then cut into chips.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

For purposes of this invention, the chemical elements are identified in accordance with the Periodic Table of the Elements reproduced in "Basic Inorganic Chemistry" by F. Albert Cotton, Geoffrey Wilkinson and Paul L. Gaus, published by John Wiley and Sons, Inc., 3rd Edition, 1995.

Certain of the following examples are provided to further illustrate this invention.

EXAMPLE 1

A 100 milliliter Parr autoclave was charged with 0.11 grams of $PdI_2$ (1000 ppm Pd), and 0.81 grams of Ligand A described herein (2 mol ligand per mole palladium). The reactor was sealed and purged with nitrogen, then 25 milliliters of dry 1,4-dioxane, 3 milliliters of butadiene, 1.2 milliliters of water (2 moles per mole butadiene) and 1.09 grams of N-methylpyrrolidinone (as an internal standard) were added via syringe. The reactor was pressurized with 1400 psi carbon monoxide, then heated to 110° C. After 2 hours reaction time, the mixture was analyzed by gas chromatography. Butadiene was 9% converted. The product mixture contained 67.5% of 3-pentenoic acid and 32.4% of 4-pentenoic acid.

EXAMPLE 2

A 100 milliliter Parr autoclave was charged with 0.05 grams of $PdCl_2$ (1000 ppm Pd), and 0.66 grams of Ligand A described herein (2 mol ligand per mole palladium). The reactor was sealed and purged with nitrogen, then 25 milliliters of dry 1,4-dioxane, 3 milliliters of butadiene, 1.2 milliliters of water (2 moles per mole butadiene) and 1.08 grams of N-methylpyrrolidinone (as an internal standard) were added via syringe. The reaction mixture was pressurized with 1000 psi carbon monoxide, and heated to 110° C. After 2 hours reaction time, the mixture was analyzed by gas chromatography. Butadiene was 22% converted. The product mixture contained 99.9% of 3-pentenoic acid.

EXAMPLE 3

A 100 milliliter Parr autoclave was charged with 0.11 grams of $PdI_2$ (1000 ppm Pd), and 0.73 grams of Ligand M described herein (3 mol ligand per mole palladium). The reactor was sealed and purged with nitrogen, then 25 milliliters of dry 1,4-dioxane, 3 milliliters of butadiene, 1.2 milliliters of water (2 moles per mole butadiene) and 1.09 grams of N-methylpyrrolidinone (as an internal standard) were added via syringe. The reactor was pressurized with 1400 psi carbon monoxide and the mixture heated to 110° C. After 2 hours reaction time, the mixture was analyzed by gas chromatography. Butadiene was 9% converted. The product mixture contained 59.2% of 3-pentenoic acid, 25.2% of 4-pentenoic acid, and 15.5% of isovaleric acid.

EXAMPLE 4

A 100 milliliter Parr autoclave was charged with 0.10 grams of $PdI_2$ (1000 ppm Pd), and 0.46 grams of Ligand F described herein (2 mol ligand per mole palladium). The reactor was sealed and purged with nitrogen, then 25 milliliters of dry 1,4-dioxane, 3 milliliters of butadiene, 1.2 milliliters of water (2 moles per mole butadiene) and 1.07 grams of N-methylpyrrolidinone (as an internal standard) were added via syringe. The reaction mixture was then pressurized with 500 psi carbon monoxide and heated to 95° C. After 2 hours reaction time, the mixture was analyzed by gas chromatography. Butadiene was 35% converted. The product mixture contained 94.5% of 3-pentenoic acid and 5.5% of 2-pentenoic acid.

EXAMPLE 5

A 100 milliliter Parr autoclave was charged with 0.10 grams of $PdI_2$ (1000 ppm Pd), and 0.47 grams of Ligand F described herein (2 mol ligand per mole palladium). The reactor was sealed and purged with nitrogen, then 25 milliliters of dry 1,4-dioxane, 3 milliliters of butadiene, 1.2 milliliters of water (2 moles per mole butadiene) and 1.08 grams of N-methylpyrrolidinone (as an internal standard) were added via syringe. The reaction mixture was pressurized with 220 psi carbon monoxide and heated to 110° C. After 2 hours reaction time, the mixture was analyzed by gas chromatography. Butadiene was 18% converted. The product mixture contained 99.9% of 3-pentenoic acids.

EXAMPLE 6

A 100 milliliter Parr autoclave was charged with 0.15 grams of palladium bis(dibenzylideneacetone) (1000 ppm Pd), and 0.44 grams of Ligand F described herein (2 mol ligand per mole palladium). The reactor was sealed and purged with nitrogen, then 25 milliliters of dry 1,4-dioxane, 34 microliters of 57% aqueous HI (1 mole iodide per mole palladium), 1 milliliter of butadiene, 0.4 milliliters of water (2 moles per mole butadiene) and 1.08 grams of N-methylpyrrolidinone (as an internal standard) were added via syringe. The reaction mixture was pressurized with 1372 psi carbon monoxide, and heated to 110° C. After 2 hours reaction time, the mixture was analyzed by gas chromatography. Butadiene was 91% converted. The product mixture contained 95.5% of 3-pentenoic acid and 3.5% of 2-pentenoic acid.

EXAMPLE 7

A 100 milliliter Parr autoclave was charged with 0.15 grams of palladium bis(dibenzylideneacetone) (1000 ppm Pd), and 0.44 grams of Ligand F described herein(2 mol ligand per mole palladium). The reactor was sealed and purged with nitrogen, then 25 milliliters of dry 1,4-dioxane, 34 microliters of 57% aqueous HI (1 mole iodide per mole palladium), 1 milliliter of butadiene, 0.4 milliliters of water (2 moles per mole butadiene) and 1.04 grams of N-methylpyrrolidinone (as an internal standard) were added via syringe. The reaction mixture was pressurized with 900 psi carbon monoxide and 200 psi $H_2$, and heated to 110° C. After 30 minutes reaction time, the mixture was analyzed by gas chromatography. Butadiene was 92% converted. The product mixture contained 92.6% by weight of 3-pentenoic acid and 7.4% by weight light by-product, possibly butane.

EXAMPLE 8

A 100 milliliter Parr autoclave was charged with 0.15 grams of palladium bis(dibenzylideneacetone) (1000 ppm Pd), and 0.44 grams of Ligand F described herein(2 mol ligand per mole palladium). The reactor was sealed and purged with nitrogen, then 25 milliliters of dry 1,4-dioxane, 0.3 milliliters of valeric acid, 3 milliliters of butadiene, 1.2 milliliters of water (2 moles per mole butadiene) and 1.08 grams of N-methylpyrrolidinone (as an internal standard) were added via syringe. The reaction mixture was pressurized with 1300 psi carbon monoxide, and heated to 110° C. After 2 hours reaction time, the mixture was analyzed by gas chromatography. Butadiene was 2% converted to 3-pentenoic acid.

EXAMPLE 9

A 160 milliliter magnetically stirred autoclave was purged with 1:1 $H_2$/CO and charged with a catalyst solution consisting of 0.15 mmol of dicarbonylacetylacetonato rhodium (I), 0.74 mmol of Ligand F described herein, and 30 milliliters of tetrahydrofuran. The autoclave was pressurized with 10 psig 1:1 $H_2$/CO and heated to 85° C. A solution of the triethylammonium salt of 3-pentenoic acid was prepared by addition of 23 mmol of triethylamine to 22 mmol of 3-pentenoic acid in 2 milliliters of tetrahydrofuran. This solution was added to the autoclave by syringe and the reaction mixture pressurized to 100 psig with 1:1 $H_2$/CO. After 170 minutes of reaction at 85° C., under 100 psi 1:1 $H_2$/CO, gas chromatography analysis of the reaction products (as their free acids) provided the following results: 88% of 5-formylvaleric acid, 7% of branched formylvaleric acids, 5% of valeric acid and 1% of 2-pentenoic acid.

EXAMPLE 10

A 160 milliliter magnetically stirred autoclave was purged with 1:1 $H_2$CO and charged with a catalyst solution consisting of 0.14 mmol of dicarbonylacetylacetonato rhodium (I), 0.60 mmol of Ligand F described herein, and 50 milliliters of tetrahydrofuran. The autoclave was pressurized with 100 psig 1:1 $H_2$CO and heated to 85° C. 20 mmol of 3-pentenoic acid was added to the autoclave by syringe and the reaction mixture pressurized to 150 psig with 1:1 $H_2$/CO. After 150 minutes of reaction at 85° C. under 150 psi 1:1 $H_2$/CO, gas chromatography analysis of the reaction products provided the following results: 75% of 5-formylvaleric acid, 6% of branched formylvaleric acids, 8% of valeric acid, 5% of 2-pentenoic acid and 4% of 3-pentenoic acid.

EXAMPLE 11

A 160 milliliter magnetically stirred autoclave was purged with $N_2$ and charged with a catalyst solution consisting of 0.15 mmol of dicarbonylacetylacetonato rhodium (I), 0.73 mmol of Ligand F described herein, and 30 milliliters of tetrahydrofuran. The autoclave was pressurized to 10 psig with $N_2$ and heated to 85° C. A solution of the triethylammonium salt of 4-pentenoic acid was prepared by addition of 21 mmol of triethylamine to 22 mmol of 4-pentenoic acid in 4 milliliters of tetrahydrofuran. This solution was added to the autoclave by syringe and the reaction mixture pressurized to 100 psig with 1:1 $H_2/CO$. After 155 minutes of reaction at 85° C., under 100 psi 1:1 $H_2/CO$, gas chromatography analysis of the reaction products (as their free acids) provided the following results: 93% of 5-formylvaleric acid, 3% of branched formylvaleric acids, 4% of valeric acid and <1% of 2-pentenoic acid.

EXAMPLE 12

A 160 milliliter magnetically stirred autoclave was purged with 1:1 H2/CO and charged with a catalyst solution consisting of 0.15 mmol of dicarbonylacetylacetonato rhodium (I), 0.66 mmol of Ligand F described herein, and 50 milliliters of tetrahydrofuran. The autoclave was pressurized to 30 psig with 1:1 $H_2/CO$ and heated to 85° C. 40 mmol of 4-pentenoic acid was added to the autoclave by syringe and the reaction mixture pressurized to 120 psig with 1:1 $H_2/CO$. The reaction was maintained at 85° C. and the autoclave periodically repressurized to 120 psig. After 220 minutes of reaction at 85° C., gas chromatography analysis of the reaction products provided the following results: 77% of 5-formylvaleric acid, 6% of branched formylvaleric acids, 9% of valeric acid, 6% of 2-pentenoic acid and 2% of 3-pentenoic acid.

EXAMPLE 13

A 160 milliliter magnetically stirred autoclave was purged with 1:1 $H_2CO$ and charged with a catalyst solution consisting of 0.14 mmol of dicarbonylacetylacetonato rhodium (I), 0 .65 mmol of Ligand F described herein, 26 mmol of benzotriazole and 50 milliliters of tetrahydrofuran. The autoclave was pressurized with 75 psig 1:1 $H_2/CO$ and heated to 85° C. 20 mmol of 3-pentenoic acid was added to the autoclave by syringe and the reaction mixture pressurized to 150 psig with 1:1 $H_2/CO$. After 105 minutes of reaction at 85° C., under 150 psi 1:1 $H_2/CO$, gas chromatography analysis of the reaction products (as their free acids) provided the following results: 73% of 5-formylvalenc acid, 8% of branched formylvaleric acids, 7% of valeric acid, 7% of 2-pentenoic acid and 4% of 3-pentenoic acid.

EXAMPLE 14

A 160 milliliter magnetically stirred autoclave was purged with $N_2$ and charged with a catalyst solution consisting of 0.15 mmol of dicarbonylacetylacetonato rhodium (I), 0.73 mmol of Ligand F described herein, and 28 milliliters of tetrahydrofuran. The autoclave was pressurized with 15 psig $N_2$ and heated to 85° C. A solution of the triethylammonium salt of trans-2-pentenoic acid was prepared by addition of 20 mmol of triethylamine to 24 mmol of trans-2-pentenoic acid in 4 milliliters of tetrahydrofuran. This solution was added to the reactor by syringe and the reaction mixture pressurized to 100 psig with 1:1 $H_2/CO$. After 145 minutes of reaction at 85° C. under 100 psi 1:1 $H_2/CO$, gas chromatography analysis of the reaction products (as their free acids) provided the following results: 9% of 5-formylvaleric acid, 1% of branched formylvaleric acids, 68% of valeric acid, 21% of 2-pentenoic acid and 1% of 3- pentenoic acid.

EXAMPLE 15

A 160 milliliter magnetically stirred autoclave was purged with $N_2$ and charged with a catalyst solution consisting of 0.15 mmol of dicarbonylacetylacetonato rhodium (I), 0.74 mmol of Ligand F described herein, and 30 milliliters of tetrahydrofuran. The autoclave was pressurized with 15 psig $N_2$ and heated to 85° C. 20 mmol of trans-2-pentenoic acid was added to the reactor by syringe and the reaction mixture pressurized to 100 psig with 1:1 $H_2/CO$. After 150 minutes of reaction at 85° C. under 100 psi 1:1 $H_2/CO$, gas chromatography analysis of the reaction products provided the following results: 5% of 5-formylvaleric acid, 2% of branched formylvaleric acids, 76% of valeric acid, 16% of 2-pentenoic acid and 1% of 3-pentenoic acid.

EXAMPLE 16

A 160 milliliter magnetically stirred autoclave was purged with 1:1 $H_2/CO$ and charged with a catalyst solution consisting of 0.15 mmol of dicarbonylacetylacetonato rhodium (I), 0.67 mmol of Ligand F described herein, 9.75 grams of 28–30% aqueous ammonium hydroxide solution (0.16 mol $NH_3$), 14.23 grams of water and 35 milliliters of tetrahydrofuran. The autoclave was pressurized to 25 psig with 1:1 $H_2/CO$ and heated to 85° C. 33 mmol of 3-pentenoic acid was added to the autoclave by syringe and the reaction mixture pressurized to 150 psig with 1:1 $H_2/CO$. After 135 minutes of reaction at 85° C., the reaction mixture was cooled and transferred to a glass bottle where two phases were allowed to separate. The bottom aqueous layer was transferred to a reactor containing 5 grams of chromium promoted Raney nickel catalyst and 20 milliliters of 28–30% aqueous ammonium hydroxide solution. The reactor was sealed, placed under 230 psig $H_2$ and the reaction mixture heated to 120° C. where the pressure was increased to 1000 psig with $H_2$. After 125 minutes of reaction at 120° C. under 1000 psig $H_2$, the reaction mixture was cooled, depressurized and sampled. Gas chromatography analysis of the solution provided the following results: 79% of valeric acid and 17% of epsilon caprolactam.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for producing one or more substituted or unsubstituted epsilon caprolactams which comprises: (a) subjecting one or more substituted or unsubstituted alkadienes to hydroxycarbonylation in the presence of a hydroxycarbonylation catalyst and neutralization with a base to produce one or more substituted or unsubstituted pentenoic acid salts; (b) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or said one or more substituted or unsubstituted epsilon caprolactam precursors to reductive amination in the presence of a reductive amination catalyst and cyclization optionally in the presence of a cyclization catalyst to produce said one or more substituted or unsubstituted epsilon caprolactams.

2. A process for producing one or more substituted or unsubstituted epsilon caprolactams which comprises: (a) subjecting one or more substituted or unsubstituted alkadienes to hydroxycarbonylation in the presence of a hydroxycarbonylation catalyst to produce one or more substituted or unsubstituted pentenoic acids; (b) subjecting said one or more substituted or unsubstituted pentenoic acids to neutralization with a base to produce one or more substituted or unsubstituted pentenoic acid salts; (c) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said one or more substituted or unsubstituted epsilon caprolactams.

3. A process for producing one or more substituted or unsubstituted epsilon caprolactams which comprises: (a) subjecting one or more substituted or unsubstituted alkadienes to hydroxycarbonylation in the presence of a hydroxycarbonylation catalyst and neutralization with ammonia to produce one or more substituted or unsubstituted pentenoic acid salts; (b) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive cyclization in the presence of a reductive cyclization catalyst to produce said one or more substituted or unsubstituted epsilon caprolactams.

4. A process for producing one or more substituted or unsubstituted epsilon caprolactams which comprises: (a) subjecting one or more substituted or unsubstituted alkadienes to hydroxycarbonylation in the presence of a hydroxycarbonylation catalyst to produce one or more substituted or unsubstituted pentenoic acids; (b) subjecting said one or more substituted or unsubstituted pentenoic acids to neutralization with ammonia to produce one or more substituted or unsubstituted pentenoic acid salts; (c) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive cyclization in the presence of a reductive cyclization catalyst to produce said one or more substituted o- unsubstituted epsilon caprolactams.

5. The process of claim 1 wherein the substituted or unsubstituted alkadiene comprises butadiene, the substituted or unsubstituted pentenoic acid comprises 3-pentenoic acid, the substituted or unsubstituted pentenoic acid salt comprises 3-pentenoic acid salt, the substituted or unsubstituted formylvalerate comprises 5-formylvaleric acid salt, and the substituted or unsubstituted epsilon caprolactam comprises epsilon caprolactam.

6. The process of claim 1 wherein the hydroformylation catalyst comprises a metal-ligand complex catalyst.

7. The process of claim 6 wherein said metal-ligand complex catalyst comprises a metal selected from the group consisting of a Group 8, 9 and 10 metal complexed with an organophosphorus ligand selected from the group consisting of a mono-, di-, tri- and poly-(organophosphine) ligand.

8. The process of claim 6 wherein said metal-ligand complex catalyst comprises a metal selected from the group consisting of a Group 8, 9 and 10 metal complexed with an organophosphorus ligand selected from the group consisting of:

(i) a triorganophosphine ligand represented by the formula:

wherein each $R^1$ is the same or different and is a substituted or unsubstituted monovalent hydrocarbon radical;

(ii) a monoorganophosphite represented by the formula:

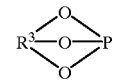

wherein $R^3$ represents a substituted or unsubstituted trivalent hydrocarbon radical containing fiom 4 to 40 carbon atoms or greater;

(iii) a diorganophosphite represented by the formula:

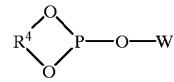

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

wherein each $R^8$ is the same or different and is a substituted or unsubstituted monovalent hydrocarbon radical; and (v) an organopolyphosphite containing two or more tertiary (trivalent) phosphorus atoms represented by the formula:

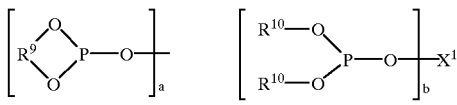

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

9. The process of claim 6 wherein said metal-ligand complex catalyst comprises a metal selected from the group consisting of a Group 8, 9 and 10 metal complexed with an organophosphorus ligand having the formula:

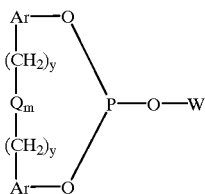

wherein W represents a substituted or unsubstituted monovalent hydrocarbon radical containing from 1 to 18 carbon atoms or greater, each Ar is the same or different and represents a substituted or unsubstituted aryl radical, each y is the same or different and is a value of 0 or 1, Q represents a divalent bridging group selected from —C($R^5$)$_2$—, —O—, —S—, —N$R^6$—, Si($R^7$)$_2$— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

10. The process of claim 6 wherein said metal-ligand complex catalyst comprises a metal selected from the group consisting of a Group 8, 9 and 10 metal complexed with an organophosphorus ligand having the formula selected from the group consisting of:

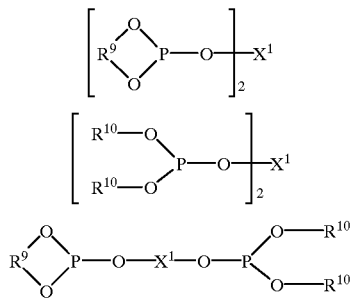

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, and each $R^{10}$ is the same or different and is a substituted or unsubstituted monovalent hydrocarbon radical containing from 1 to 24 carbon atoms.

11. The process of claim 6 wherein said metal-ligand complex catalyst comprises a metal selected from the group consisting of a Group 8, 9 and 10 metal complexed with an organophosphorus ligand having the formula selected from the group consisting of:

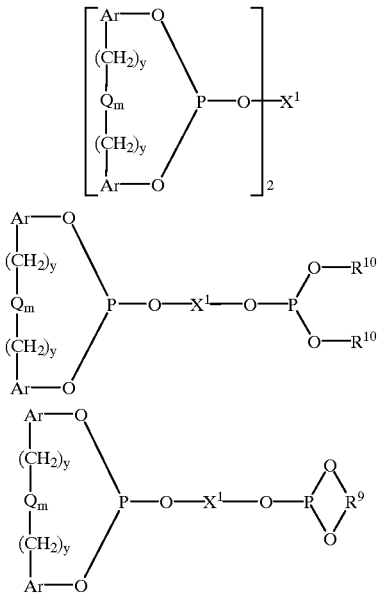

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, each Ar is the same or different and represents a substituted or unsubstituted aryl radical, each y is the same or different and is a value of 0 or 1, Q represents a divalent bridging group selected from —C($R^5$)$_2$—, —O—, —S—, —N$R^6$—, Si($R^7$)$_2$— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

12. The process of claim 1 wherein the reaction is conducted in the presence of an olefin and an aldehyde of the olefin is also produced.

13. The process of claim 1 which is conducted at a temperature from about 50° C. to 150° C. and at a total pressure from about 200 psig to about 1000 psig.

14. A process for producing a batchwise or continuously generated reaction mixture comprising:

(1) one or more substituted or unsubstituted epsilon caprolactams;

(2) optionally one or more substituted or unsubstituted formylvaleric acid salts and/or one or more substituted or unsubstituted epsilon caprolactam precursors;

(3) optionally one or more substituted or unsubstituted pentenoic acid salts;

(4) optionally one or more substituted or unsubstituted pentenoic acids; and (5) one or more substituted or unsubstituted butadienes; wherein the weight ratio of component (1) to the sum of components (2), (3) and (4) is greater than about 0.1; and the weight ratio of component (5) to the sum of components (1), (2), (3) and (4) is about 0 to about 100;

which process comprises: (a) subjecting one or more substituted or unsubstituted butadienes to hydroxycarbonylation in the presence of a hydroxycarbonylation catalyst and neutralization with a base to produce one or more substituted or unsubstituted pentenoic acid salts; (b) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said batchwise or continuously generated reaction mixture.

15. A process for producing a batchwise or continuously generated reaction mixture comprising:

(1) one or more substituted or unsubstituted epsilon caprolactams;

(2) optionally one or more substituted or unsubstituted formylvaleric acid salts and/or one or more substituted or unsubstituted epsilon caprolactam precursors;

(3) optionally one or more substituted or unsubstituted pentenoic acid salts;

(4) optionally one or more substituted or unsubstituted pentenoic acids; and (5) one or more substituted or unsubstituted butadienes; wherein the weight ratio of component (1) to the sum of components (2), (3) and (4) is greater than about 0.1; and the weight ratio of component (5) to the sum of components (1), (2), (3) and (4) is about 0 to about 100;

which process comprises: (a) subjecting one or more substituted or unsubstituted butadienes to hydroxycarbonylation in the presence of a hydroxycarbonylation catalyst to produce one or more substituted or unsubstituted pentenoic acids; (b) subjecting said one or more substituted or unsubstituted pentenoic acids to neutralization with a base to produce one or more substituted or unsubstituted pentenoic acid salts; (c) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said batchwise or continuously generated reaction mixture.

16. A process for producing a batchwise or continuously generated reaction mixture comprising:

(1) one or more substituted or unsubstituted epsilon caprolactams;

(2) optionally one or more substituted or unsubstituted formylvaleric acid salts and/or one or more substituted or unsubstituted epsilon caprolactam precursors;

(3) optionally one or more substituted or unsubstituted pentenoic acid salts;

(4) optionally one or more substituted or unsubstituted pentenoic acids; and (5) one or more substituted or unsubstituted butadienes; wherein the weight ratio of component (1) to the sum of components (2), (3) and (4) is greater than about 0.1; and the weight ratio of component (5) to the sum of components (1), (2), (3) and (4) is about 0 to about 100;

which process comprises: (a) subjecting one or more substituted or unsubstituted butadienes to hydroxycarbonylation in the presence of a hydroxycarbonylation catalyst and neutralization with ammonia to produce one or more substituted or unsubstituted pentenoic acid salts; (b) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive cyclization in the presence of a reductive cyclization catalyst to produce said batchwise or continuously generated reaction mixture.

17. A process for producing a batchwise or continuously generated reaction mixture comprising:

(1) one or more substituted or unsubstituted epsilon caprolactams;

(2) optionally one or more substituted or unsubstituted formylvaleric acid salts and/or one or more substituted or unsubstituted epsilon caprolactam precursors;

(3) optionally one or more substituted or unsubstituted pentenoic acid salts;

(4) optionally one or more substituted or unsubstituted pentenoic acids; and (5) one or more substituted or unsubstituted butadienes; wherein the weight ratio of component (1) to the sum of components (2), (3) and (4) is greater than about 0.1; and the weight ratio of component (5) to the sum of components (1), (2), (3) and (4) is about 0 to about 100;

which process comprises: (a) subjecting one or more substituted or unsubstituted butadienes to hydroxycarbonylation in the presence of a hydroxycarbonylation catalyst to produce one or more substituted or unsubstituted pentenoic acids; (b) subjecting said one or more substituted or unsubstituted pentenoic acids to neutralization with ammonia to produce one or more substituted or unsubstituted pentenoic acid salts; (c) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive cyclization in the presence of a reductive cyclization catalyst to produce said batchwise or continuously generated reaction mixture.

18. A process for producing a reaction mixture comprising one or more substituted or unsubstituted epsilon caprolactams which process comprises: (a) subjecting one or more substituted or unsubstituted alkadienes to hydroxycarbonylation in the presence of a hydroxycarbonylation catalyst and neutralization with a base to produce one or more substituted or unsubstituted pentenoic acid salts; (b) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said reaction mixture comprising one or more substituted or unsubstituted epsilon caprolactams.

19. A process for producing a reaction mixture comprising one or more substituted or unsubstituted epsilon caprolactams, which process comprises: (a) subjecting one or more substituted or unsubstituted alkadienes to hydroxycarbonylation in the presence of a hydroxycarbonylation catalyst to produce one or more substituted or unsubstituted pentenoic acids; (b) subjecting said one or more substituted or unsubstituted pentenoic acids to neutralization with a base to produce one or more substituted or unsubstituted pentenoic acid salts; (c) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive amination in the presence of a reductive amination catalyst and cyclization optionally in the presence of a cyclization catalyst to produce said reaction mixture comprising one or more substituted or unsubstituted epsilon caprolactams.

20. A process for producing a reaction mixture comprising one or more substituted or unsubstituted epsilon caprolactams which process comprises: (a) subjecting one or more substituted or unsubstituted alkadienes to hydroxycarbonylation in the presence of a hydroxycarbonylation catalyst and neutralization with ammonia to produce one or more substituted or unsubstituted pentenoic acid salts; (b) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive cyclization in the presence of a reductive cyclization catalyst to produce said reaction mixture comprising one or more substituted or unsubstituted epsilon caprolactams.

21. A process for producing a reaction mixture comprising one or more substituted or unsubstituted epsilon caprolactams which process comprises: (a) subjecting one or more substituted or unsubstituted alkadienes to hydroxycarbonylation in the presence of a hydroxycarbonylation catalyst to produce one or more substituted or unsubstituted pentenoic acids; (b) subjecting said one or more substituted or unsubstituted pentenoic acids to neutralization with ammonia to produce one or more substituted or unsubstituted pentenoic acid salts; (c) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (d) subjecting said one or more substituted or unsubstituted formylvaleric acid salts and/or one or more substituted or unsubstituted epsilon caprolactam precursors to reductive cyclization in the presence of a reductive cyclization catalyst to produce said reaction mixture comprising one or more substituted or unsubstituted epsilon caprolactams.

22. A batchwise or continuously generated reaction mixture comprising:

(1) one or more substituted or unsubstituted epsilon caprolactams;

(2) optionally one or more substituted or unsubstituted formylvaleric acid salts and/or one or more substituted or unsubstituted epsilon caprolactam precursors;

(3) optionally one or more substituted or unsubstituted pentenoic acid salts;

(4) optionally one or more substituted or unsubstituted pentenoic acids; and (5) one or more substituted or unsubstituted butadienes;

wherein the weight ratio of component (1) to the sum of components (2), (3) and (4) is greater than about 0.1; and the weight ratio of component (5) to the sum of components (1), (2), (3) and (4) is about 0 to about 100.

* * * * *